(12) United States Patent
Rudolph et al.

(10) Patent No.: US 7,906,684 B2
(45) Date of Patent: Mar. 15, 2011

(54) ANTIOXIDANTS

(75) Inventors: Thomas Rudolph, Darmstadt (DE); Herwig Buchholz, Frankfurt (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 184 days.

(21) Appl. No.: 12/298,137

(22) PCT Filed: Apr. 5, 2007

(86) PCT No.: PCT/EP2007/003109
§ 371 (c)(1), (2), (4) Date: Oct. 23, 2008

(87) PCT Pub. No.: WO2007/121845
PCT Pub. Date: Nov. 1, 2007

(65) Prior Publication Data
US 2009/0246158 A1    Oct. 1, 2009

(30) Foreign Application Priority Data

Apr. 25, 2006  (DE) .................. 10 2006 019 044

(51) Int. Cl.
| C07C 49/00 | (2006.01) |
| C07C 205/00 | (2006.01) |
| C07C 33/00 | (2006.01) |
| A61K 31/12 | (2006.01) |
| A61K 8/00 | (2006.01) |
| C23F 11/00 | (2006.01) |

(52) U.S. Cl. ......... 568/331; 568/334; 568/705; 568/811; 514/685; 514/730; 514/739; 424/62; 252/396

(58) Field of Classification Search ............... 568/331, 568/334, 705, 811; 514/685, 730, 739
See application file for complete search history.

(56) References Cited

U.S. PATENT DOCUMENTS

| 3,835,095 A | 9/1974 | De Jonge et al. |
| 5,880,301 A * | 3/1999 | Shibasaki et al. ............. 556/21 |
| 6,066,327 A | 5/2000 | Gubernick et al. |
| 6,486,366 B1 * | 11/2002 | Ostgard et al. ............... 568/863 |

FOREIGN PATENT DOCUMENTS

| GB | 1 345 988 A | 2/1974 |
| JP | 56-22711 A | 3/1981 |
| JP | 1-151530 A | 6/1989 |
| JP | 2-160737 A | 6/1990 |
| WO | WO 2004/046334 A2 | 6/2004 |
| WO | WO 2005/004630 A1 | 1/2005 |

OTHER PUBLICATIONS

"Antioxidantien", CD Römpp Chemie Lexikon, Version 1.0, Stuttgart/New York, Georg Thieme Verlage 1995.

* cited by examiner

*Primary Examiner* — Sikarl A Witherspoon
(74) *Attorney, Agent, or Firm* — Millen, White, Zelano & Branigan, P.C.

(57) ABSTRACT

The present invention relates to the use of compounds of the formula (I) where R stands for [lacuna] with radicals defined in the description, as antioxidants, to corresponding novel compounds and compositions, and to corresponding processes for the preparation of compounds and compositions.

25 Claims, 1 Drawing Sheet

ANTIOXIDANTS

The present invention relates to the use of compounds as antioxidant or for product protection or for pigmentation control, to corresponding novel compounds and compositions, and to corresponding processes for the preparation of compounds and compositions.

One area of application of the compounds according to the invention is, for example, cosmetics. The object of care cosmetics is wherever possible to obtain the impression of youthful skin. In principle, there are various ways of achieving this object. For example, existing skin damage, such as irregular pigmentation or the formation of wrinkles, can be compensated for by covering powders or creams. Another approach is to protect the skin against environmental influences which lead to permanent damage and thus ageing of the skin. The idea is therefore to intervene in a preventative manner and thus to delay the ageing process. An example of this are UV filters, which, as a result of absorption of certain wavelength ranges, prevent or at least reduce skin damage. Whereas in the case of UV filters the damaging event, the UV radiation, is screened off by the skin, another route involves attempting to support the skin's natural defence or repair mechanisms against the damaging event. Finally, a further approach involves compensating for the weakening of the defence functions of the skin against harmful influences with increasing age by externally supplying substances which are able to replace this diminishing defence or repair function. For example, the skin has the ability to scavenge free radicals generated by external or internal stress factors. This ability diminishes with increasing age, causing the ageing process to accelerate with increasing age.

A further difficulty in the preparation of cosmetics is that active compounds which are intended to be incorporated into cosmetic compositions are frequently unstable and can be damaged in the composition. The damage may be caused, for example, by a reaction with atmospheric oxygen or by absorption of UV rays. The molecules damaged in this way may, for example, change their colour and/or lose their activity through their structural change. Corresponding difficulties generally occur in the preparation, storage or use of compositions comprising oxidation-sensitive ingredients.

A known way of dealing with the problems described consists in adding antioxidants to the compositions.

According to CD Römpp Chemie Lexikon [CD Römpp's Lexicon of Chemistry]—Version 1.0, Stuttgart/New York: Georg Thieme Verlag 1995, anti-oxidants are compounds which inhibit or prevent undesired changes in the substances to be protected caused by the action of oxygen, inter alia oxidative processes. Areas of application are, for example, in plastics and rubber for protection against ageing; in fats for protection against rancidity, in oils, cattle feeds, automotive gasoline and jet fuels for protection against gumming, in transformer and turbine oil against sludge formation, in flavours against odour impairment. Compounds that are effective as antioxidants are, inter alia, phenols, hydroquinones, pyrocatechols, aromatic compounds, amines, each of which are substituted by sterically hindering groups, and metal complexes thereof. According to Römpp, the action of the antioxidants usually consists in that they act as free-radical scavengers for the free radicals which arise during autoxidation.

However, there continues to be a demand for skin-tolerated antioxidants which are also suitable for use in skin-care compositions.

The object of the invention is therefore to provide a composition which has a protective action against UV rays and/or exerts a protective action against oxidative stress on body cells and/or counters skin ageing.

The present invention therefore relates firstly to the use of compounds of the formula I

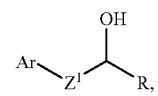

where
R stands for

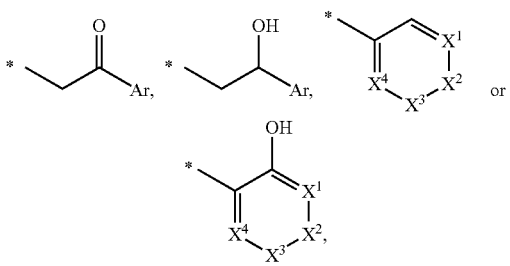

where the radicals Ar each, independently of one another, stand for an un-substituted or mono- or polysubstituted aromatic ring or condensed ring system having 6 to 18 C atoms, at least one ring of which has aromatic character, in which, in addition, one or two CH groups per ring may also be replaced by C=O, N, O or S and in a condensed ring system, in addition, one or two $CH_2$ groups may be replaced by C=O or C=$CH_2$, $Z^1$ stands for $CR^7R^8$ or a single bond, $X^1$ to $X^4$ are each selected, independently of one another, from C—$R^1$, O, N or S, where 2 adjacent radicals from $X^1$ to $X^4$ may together also stand for an unsubstituted or mono- or polysubstituted ring or condensed ring system having 6 to 18 C atoms, at least one ring of which preferably has aromatic character, in which, in addition, one or two CH groups per ring may be replaced by C=O, N, O or S and in a condensed ring system, in addition, one or two $CH_2$ groups may be replaced by C=O or C=$CH_2$, $R^1$ is selected from H, straight-chain or branched $C_1$- to $C_{20}$-alkoxy groups, where the alkyl chains may each also be interrupted by oxygen or nitrogen, straight-chain or branched $C_1$- to $C_{20}$-alkyl groups, where the alkyl chains may each also be interrupted by oxygen or nitrogen, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chains may each also be interrupted by oxygen or nitrogen, straight-chain or branched $C_1$- to $C_{20}$-hydroxyalkoxy groups, where the hydroxyl group(s) may be bonded to primary or secondary carbon atoms of the chain and furthermore the alkyl chain may also be interrupted by oxygen, straight-chain or branched $C_1$- to $C_{20}$-alkylamino groups, straight-chain or branched $C_1$- to $C_{20}$-dialkylamino groups, or $R^1$ stands for a carboxylic acid, phosphoric acid, sulfonic acid, sulfuric acid or sulfone function, which may optionally be esterified or alkylated by means of straight-chain or branched $C_1$- to $C_{20}$-alkyl groups or straight-chain or branched $C_3$- to $C_{20}$-alkenyl groups, $R^7$ and $R^8$ are each selected, independently of one another, from H, OH, straight-chain or branched $C_1$- to $C_{20}$-alkoxy groups, straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, straight-chain or branched $C_1$- to $C_{20}$-hydroxyalkoxy groups, where the hydroxyl group(s) may be bonded to primary or secondary carbon atoms of the chain and furthermore the alkyl chain may also be interrupted by oxygen, or salts of the compounds of the formula I as antioxidant.

It is preferred here for the compounds of the formula I to be compounds of the formula Ia, Ib, Ic or Id

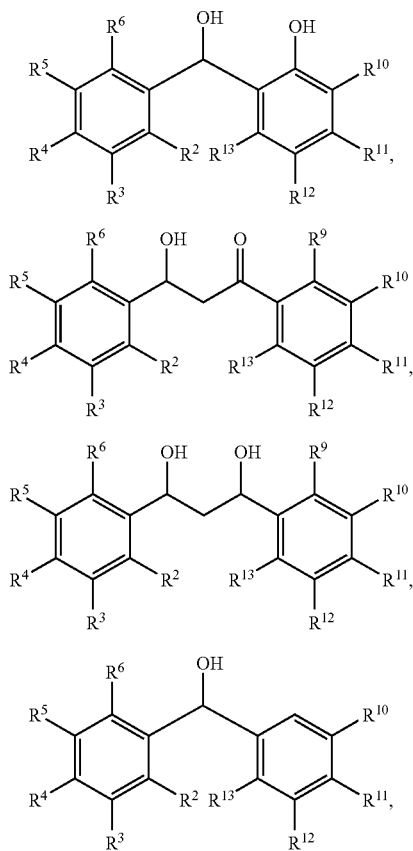

where $R^2$ to $R^6$ and $R^9$ to $R^{13}$ are each selected, independently of one another, from H,

OH, straight-chain or branched $C_1$- to $C_{20}$-alkoxy groups, where the alkyl chains may each also be interrupted by oxygen or nitrogen, straight-chain or branched $C_1$- to $C_{20}$-alkyl groups, where the alkyl chains may each also be interrupted by oxygen or nitrogen, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chains may each also be interrupted by oxygen or nitrogen, straight-chain or branched $C_1$- to $C_{20}$-hydroxyalkoxy groups, where the hydroxyl group(s) may be bonded to primary or secondary carbon atoms of the chain and furthermore the alkyl chain may also be interrupted by oxygen, straight-chain or branched $C_1$- to $C_{20}$-alkylamino groups, straight-chain or branched $C_1$- to $C_{20}$-dialkylamino groups, or $R^2$ to $R^6$ and $R^9$ to $R^{13}$ each stand, independently of one another, for a carboxylic acid, phosphoric acid, sulfonic acid, sulfuric acid or sulfone function, which may optionally be esterified or alkylated by means of straight-chain or branched $C_1$- to $C_{20}$-alkyl groups or straight-chain or branched $C_3$- to $C_{20}$-alkenyl groups, or salts of the compounds of the formulae Ia to Id.

Counterions which can be employed for the salts here are all anions which are acceptable for the corresponding application. It is advantageous here for the salts to be strong acids. It is particularly preferred in accordance with the invention for the salts to be chlorides or bromides.

In accordance with the invention, the compounds described can be used as active compound for topical application or for the preparation of cosmetic, dermatological or pharmaceutical compositions or for the preparation of household products. They can also be used for the preparation of foods or food supplements. The compounds described can be employed for product protection. For the purposes of this application, product protection means, in particular, the protection of oxidation-sensitive formulation constituents, such as organic or inorganic dyes, antioxidants, vitamins, perfume components, oil components or matrix constituents, such as emulsifiers, thickeners, film formers and surfactants. This application relates to the corresponding use.

The invention also relates to the use of the compounds for the preparation of cosmetic or pharmaceutical, in particular dermatological compositions or of foods or food supplements or for the preparation of household products.

Preference is given here to the use of compounds of the formula I or of the formulae Ia to Id in which $R^4$ to $R^{11}$ are each selected, independently of one another, from H, straight-chain or branched $C_1$- to $C_{20}$-alkoxy groups, straight-chain or branched $C_1$- to $C_{20}$-alkyl groups or straight-chain or branched $C_1$- to $C_{20}$-dialkylamino groups.

$R^4$ and $R^{11}$ are each particularly preferably selected, independently of one another, from H, straight-chain or branched $C_1$- to $C_4$-alkoxy groups, in particular methoxy, isopropoxy and tert-butoxy, straight-chain or branched $C_1$- to $C_6$-alkyl groups, in particular methyl, isopropyl and tert-butyl, and $C_1$- to $C_4$-dialkylamino groups, in particular dimethylamino or diethylamino.

Preference is given here to the use of compounds of the formula I or of the formulae Ia to Id in which $R^3$, $R^5$, $R^9$, $R^{10}$ and $R^{12}$ denote H.

A further preferred group of compounds are compounds of the formula I or of the formulae Ia to Id in which $R^3$ and $R^{12}$ each, independently of one another, denote H, $SO_3H$ or sulfonate. $R^{12}$ is very particularly preferably $SO_3H$.

Preference is given here to the use of compounds of the formula I or of the formulae Ia to Id in which $R^2$, $R^6$ and $R^{13}$ denote H.

Further combinations are disclosed in the Claims.

In a variant of the invention, particular preference may be given to the use of at least one compound of the formula I or of the formulae Ia to Id which is characterised in that $R^4$ is selected from H, $C_1$- to $C_4$-alkoxy groups or $C_1$- to $C_4$-dialkylamino groups, $R^{11}$ is selected from straight-chain or branched $C_1$- to $C_6$-alkyl groups, $C_1$- to $C_4$-dialkylamino groups or $C_1$- to $C_4$-alkoxy groups.

In a variant of the invention, particular preference may be given to the use of at least one compound of the formula I or of the formulae Ia to Id which is characterised in that $R^6$ denotes $C_1$- to $C_{10}$-alkoxycarbonyl.

In a variant of the invention, particular preference may be given to the use of at least one compound of the formula I or of the formulae Ia to Id which is characterised in that at least one group from $R^2$, $R^6$ and $R^{13}$ stands for OH. These compounds exhibit a particularly pronounced antioxidative performance.

In a further variant of the invention, particular preference may be given to the use of at least one compound of the formula I or of the formulae Ia to Id which is characterised in that at least one group from $R^4$ and $R^{11}$ stands for t-butyl.

In accordance with the invention, preference may furthermore be given to the use of at least one compound of the formula I or of the formulae Ia to Id containing long-chain hydrocarbon radicals, in particular branched long-chain hydrocarbon radicals. These compounds are often particularly readily miscible with vehicle substances, such as, in particular, oils, and can thus be employed particularly easily in formulations. In this variant of the invention, it is particularly preferred for at least one radical from $R^2$ to $R^6$ and $R^9$ to $R^{13}$ to stand for a branched or unbranched $C_{7-30}$-alkyl or $C_{6-30}$-hydroxyalkyl radical or an ester or ether containing a radical of this type.

In a further variant of the invention, it may be preferred to use compounds of the formula I or of the formulae Ia to Id which are characterised in that $R^4$ stands for a branched or unbranched $C_{1-20}$-alkoxy or branched or unbranched $C_{2-20}$-alkyleneoxy spacer, which is bonded via an Si atom to an oligo- or polysiloxane chain which contains one or more compounds of the formula I, where $R^4$ preferably stands for a propanyloxy, isopropanyloxy, propenyloxy, isopropenyloxy or in particular an allyloxy spacer, where a silicon atom is preferably bonded to the 1-C or to the 2-C of the spacer double bond.

Particular preference is given here to the use of at least one compound of the formula I or of the formulae Ia to Id which is selected from 2-(hydroxyphenylmethyl)-5-diethylaminophenol, 2-(hydroxyphenylmethyl)phenol, 2-(hydroxyphenylmethyl)-5-sulfophenol, 2-(hydroxyphenylmethyl)-5-methoxy-4-sulfophenol, 2-(hydroxyphenylmethyl)-5-methoxyphenol, ethyl 2-[(4-diethylamino-2-hydroxyphenyl)hydroxymethyl]benzoate, hexyl 2-[(4-diethylamino-2-hydroxyphenyl)hydroxymethyl]benzoate, ethyl hexyl 2-[(4-diethylamino-2-hydroxyphenyl)hydroxymethyl]benzoate, ethylhexyl 2-[(2-hydroxyphenyl)hydroxymethyl]benzoate, 3-hydroxy-1,3-diphenylpropan-1-one, 1-(4-tert-butylphenyl)-3-hydroxy-3-phenylpropan-1-one, 1-(4-tert-butylphenyl)-3-hydroxy-3-(4-methoxyphenyl)propan-1-one, 3-(4-tert-butylphenyl)-3-hydroxy-1-phenylpropan-1-one, 3-(4-tert-butylphenyl)-3-hydroxy-1-(4-methoxyphenyl)propan-1-one or 3-(4-methoxyphenyl)-3-hydroxy-1-(4-methoxyphenyl)propan-1-one.

The present invention furthermore relates to the novel compounds of the formula I.

These are compounds of the formula Ib or Ic

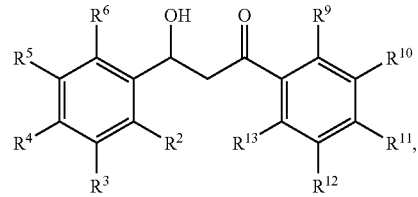
(Ib)

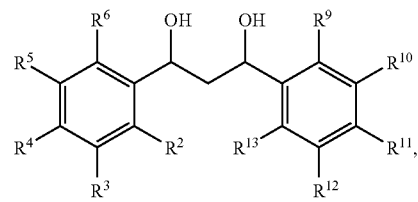
(Ic)

where $R^4$ and $R^{11}$ each, independently of one another, denote H, a straight-chain or branched $C_1$- to $C_{20}$-alkyl group, a straight-chain or branched $C_1$- to $C_{20}$-alkoxy group or a straight-chain or branched $C_1$- to $C_{20}$-dialkylamino group, $R^6$ denotes H or a carboxylic acid, phosphoric acid, sulfonic acid, sulfuric acid or sulfone function, which may be esterified or alkylated by means of straight-chain or branched $C_1$- to $C_{20}$-alkyl groups or straight-chain or branched $C_3$- to $C_{20}$-alkenyl groups, and $R^2$, $R^3$, $R^5$, $R^9$, $R^{10}$ $R^{12}$ and $R^{13}$ denote H.

Selected preferred compounds are the compounds of the formulae (1) to (6):

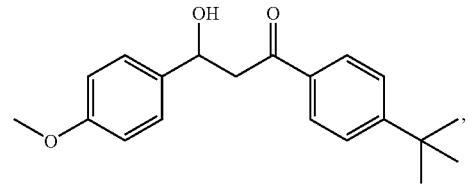
(1)

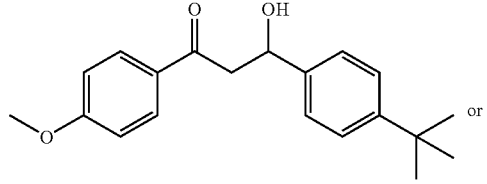
(2)
or

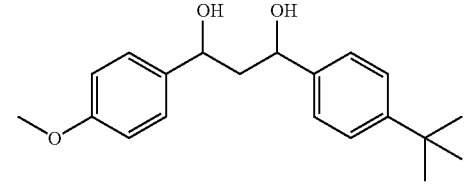
(3)

or salts of the compounds, and

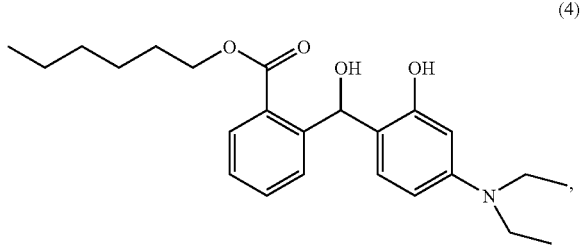
(4)

-continued

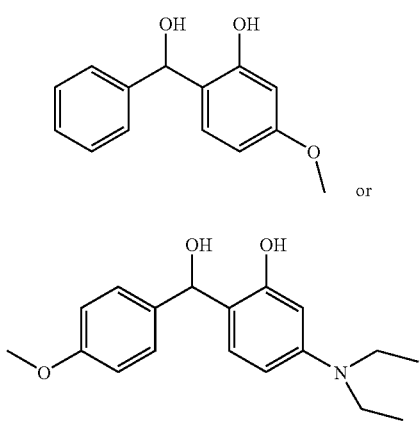

or salts of the compounds.

A particularly suitable group of compounds which can be used in accordance with the invention are, besides the compounds of the formulae (1) to (6), also the compounds of the formulae (7) to (15)

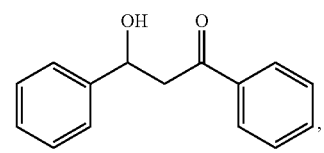

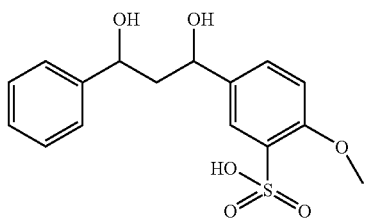

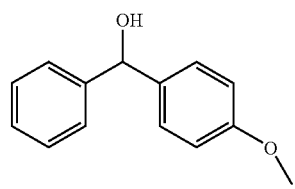

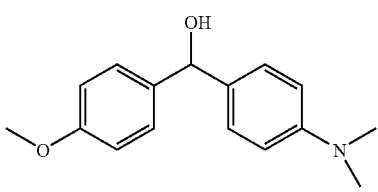

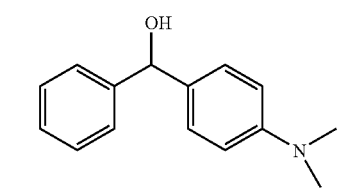

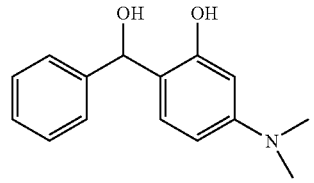

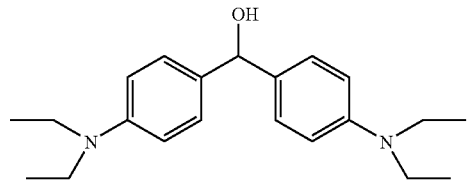

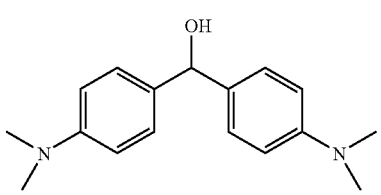

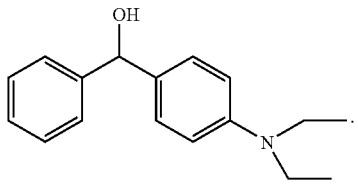

The invention furthermore relates to compositions comprising at least one compound of the formula I or of the formulae Ia to Id. The compositions are usually either compositions which can be applied topically, for example cosmetic or dermatological formulations, or foods or food supplements or household products. In this case, the compositions comprise a vehicle which is suitable cosmetically or dermatologically, for foods or household products and, depending on the desired property profile, optionally further suitable ingredients.

For the purposes of the present invention, the term formulation is also used synonymously with the term composition.

Advantages of the compounds according to the invention or the use of compounds according to the invention or the compositions according to the invention may, in particular, be the following:

an antioxidant action against free radicals, which are induced, for example, by UV light or thermolytic processes, such as smoking, such as, for example, against the superoxide free-radical anion or the NO free radical, or against reactive oxygen species, such as, for example, against singlet oxygen and peroxides, preferred compounds combine a strong antioxidant activity with high molecular stability, a product-stabilising action on cosmetic, pharmaceutical, in particular dermatological products or household products or foods and food supplements, in particular those which comprise dyes, consistency substances or odour substances, preferred compounds of the formula I are suitable as oil component in compositions, preferred compounds of the formula I are suitable for improving pharmaceutical properties, such as, for example, the skin feel, of compositions, preferred compounds of the formula I exhibit good solubility and solvent properties, preferably, for example, as solvents for crystalline components, a preferred group of compounds according to the invention can also cause skin tanning or improve the action of skin-tanning substances, such as dihydroxyacetone, well tolerated by the skin, a product-stabilising action on pigments and surface coatings, preferred compounds of the formula I are suitable for the production or boosting of light protection factors, such as LSF, SPF, PPD or IPD, or free-radical protection factors, a stabilising action on autooxidisable polyethylene glycol (PEG) or polyglycerin (PG) derivatives, such as, in particular, PEG- or PG-containing emulsifiers, as mentioned below in this application, or a reduction in the damaging action of the degradation products of autooxidisable polyethylene glycol (PEG) or polyglycerin (PG) derivatives, a stabilising action on dyes, consistency substances or odour substances, or on antioxidants or vitamins, and UV filters as well as titanium dioxide-containing pigments, in particular in cosmetic, pharmaceutical, in particular dermatological products or household products or foods and food supplements, while most antioxidants become ineffective after reaction with free radicals, preferred compounds of the formula I exhibit a UV-filtering action after this reaction and thus continue their protective function, preferred compounds according to the invention having antioxidant properties can also be employed for pigmentation control since they can have a lightening action on skin areas.

In addition, preferred compounds of those described here are colourless or only weakly coloured and thus do not result in discoloration of the compositions, or only do so to a minor extent.

As already stated above, the present invention furthermore relates to compositions comprising at least one vehicle which is suitable for cosmetic or dermatological compositions or household products and at least one compound of the above-mentioned formula I.

In accordance with the invention, it may be particularly preferred here for the composition to comprise at least one compound of the formula I en

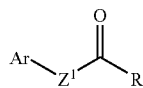

I en where the radicals Ar, $Z^1$ and R each, independently of one another and independently of the radicals of the compounds of the formula I, have the meaning indicated above for the compounds of the formula I.

It is particularly preferred here for the composition to comprise at least one compound of the formula Ia en, Ib en or Id en

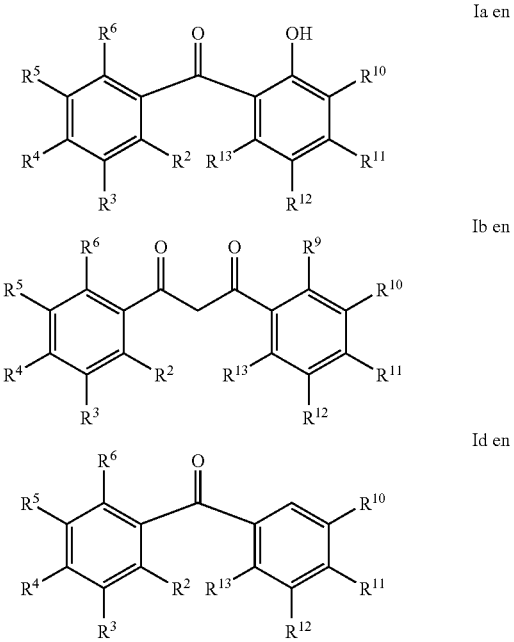

Ia en

Ib en

Id en where the radicals $R^1$-$R^6$ and $R^9$-$R^{13}$ each, independently of one another and independently of the radicals of the compounds of the formula Ia, Ib, Ic or Id, have the meaning indicated above for the compounds of the formulae Ia, Ib, Ic and Id.

It is particularly preferred here for the radicals in the at least one compound of the formula I and the at least one compound of the formula I en or the at least one compound of the formulae Ia to Id and the at least one compound of the formula Ia en, Ib en or Id en to be identical. In this case, the compound of the formula I can simultaneously serve as reservoir for the UV absorption potential of the compound of the formula I en, i.e. the use of the compounds of the formula I thus enables a reduction in the use concentration of the UV filter of the formula I en. Tailoring of the use concentrations presents the person skilled in the art with absolutely no difficulties.

The compounds of the formula I or Ia, Ib, Ic or Id are, in accordance with the invention, typically employed in amounts of 0.01 to 20% by weight, preferably in amounts of 0.1% by weight to 10% by weight and particularly preferably in amounts of 1 to 8% by weight. The person skilled in the art is presented with absolutely no difficulties here in selecting the amounts correspondingly depending on the intended action of the composition.

In order that the compounds according to the invention or the compounds of the formula I or of the formulae Ia to Id to be used in accordance with the invention are able to develop their positive action as free-radical scavengers on the skin particularly well in a composition, it may be preferred to allow the compounds according to the invention to penetrate into deeper skin layers. Several possibilities are available for this purpose. Firstly, the compounds according to the invention can have an adequate lipophilicity in order to be able to penetrate through the outer skin layer into epidermal layers. As a further possibility, corresponding transport agents, for example liposomes, which enable transport of the compounds according to the invention through the outer skin layers may also be provided in the composition. Finally, systemic transport of the compounds according to the invention is also conceivable. The composition is then designed, for example, in such a way that it is suitable for oral administration.

In general, the substances of the formula I act as free-radical scavengers. Free radicals of this type are generated exogenously not only by sunlight, but also by the action of reactive substances, such as ozone, nitrogen oxides (for example cigarette smoke), or exposure to heavy metals (for example in the food). Further examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leukocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

Owing to these properties, the compounds according to the invention or the compounds of the formula I or of the formulae Ia to Id to be used in accordance with the invention are, in a composition, generally also suitable for immune protection and for the protection of DNA and RNA. In particular, the compounds or the compounds of the formula I or of the formulae Ia to Id to be used in accordance with the invention are, in a composition, suitable for the protection of DNA and RNA against oxidative attack, against free radicals and against damage due to radiation, in particular UV radiation. A further advantage of the compounds according to the invention or compounds of the formula I or of the formulae Ia to Id to be used in accordance with the invention is, in a composition, cell protection, in particular protection of Langerhans cells against damage due to the above-mentioned influences. All these uses and the use of the compounds according to the invention for the preparation of compositions which can be employed correspondingly are expressly also a subject-matter of the present invention.

In particular, preferred compounds of the formula I or of the formulae Ia to Id and compositions comprising these compounds are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplakia, leukoplakiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, for the treatment of skin problems caused by UV radiation.

The antioxidant actions of the compounds of the formula I or of the formulae Ia to Id can be demonstrated, for example, by means of the 2,2-diphenyl-1-picrylhydrazyl (DPPH) assay. 2,2-Diphenyl-1-picrylhydrazyl is a free radical which is stable in solution. The unpaired electron results in a strong absorption band at 515 nm, the solution has a dark-violet colour. In the presence of a free-radical scavenger, the electron is paired, the absorption disappears, and the decoloration proceeds stoichiometrically taking into account the electrons taken up. The absorbance is measured in a photometer. The anti-free-radical property of the substance to be tested is determined by measuring the concentration at which 50% of the 2,2-diphenyl-1-picrylhydrazyl employed has reacted with the free-radical scavenger. This concentration is expressed as $EC_{50}$, a value which should be regarded as a property of the substance under the given measurement conditions. The substance investigated is compared with a standard (for example tocopherol). The $EC_{50}$ value here is a measure of the capacity of the respective compound to scavenge free radicals. The lower the $EC_{50}$ value, the higher the capacity to scavenge free radicals. For the purposes of this invention, the expression "a large or high capacity to scavenge free radicals" is used if the $EC_{50}$ value is lower than that of tocopherol.

A further important aspect for the action of the antioxidants is the time in which this $EC_{50}$ value is achieved. This time, measured in minutes, gives the $T_{EC50}$ value, which allows a conclusion to be drawn on the rate at which these antioxidants scavenge free radicals. For the purposes of these inventions, antioxidants which achieve this value within less than 60 minutes are regarded as fast, those which only achieve the $EC_{50}$ value after more than 120 minutes are regarded as having a time-delayed action.

The anti-free-radical efficiency (AE) (described in C. Sanchez-Moreno, J. A. Larrauri and F. Saura-Calixto in J. Sci. Food Agric. 1998, 76(2), 270-276) is given by the above-mentioned quantities in accordance with the following relationship:

$$AE = \frac{1}{EC_{50}T_{EC50}}$$

A low AE (×10³) is in the range up to about 10, a moderate AE is in the range from 10 to 20 and a high AE has in accordance with the invention values above 20.

It may be particularly preferred here to combine fast-acting antioxidants with those having a slow or time-delayed action. Typical weight ratios of the fast-acting antioxidants to time-delayed antioxidants are in the range 10:1 to 1:10, preferably in the range 10:1 to 1:1, and for skin-protecting compositions particularly preferably in the range 5:1 to 2:1. In other likewise preferred compositions, however, it may be advantageous for the purposes of action optimisation for more time-delayed antioxidants than fast-acting antioxidants to be present. Typical compositions then exhibit weight ratios of the fast-acting antioxidants to time-delayed antioxidants in the range 1:1 to 1:10, preferably in the range 1:2 to 1:8.

The protective action against oxidative stress or against the effect of free radicals can thus be further improved if the compositions comprise one or more further antioxidants, the person skilled in the art being presented with absolutely no difficulties in selecting suitably fast-acting or time-delayed antioxidants.

In a preferred embodiment of the present invention, the composition is therefore a composition for the protection of body cells against oxidative stress, in particular for reducing skin ageing, characterised in that it preferably comprises one or more further antioxidants besides the one or more compounds of the formula I or of the formulae Ia to Id.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to pmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO₄), selenium and derivatives thereof (for example selenomethionine), stilbenes and derivatives thereof (for example stilbene oxide, trans-stilbene oxide).

Suitable antioxidants are also described in WO 2006/111233 and WO 2006/111234.

Suitable antioxidants are also compounds of the general formula A or B

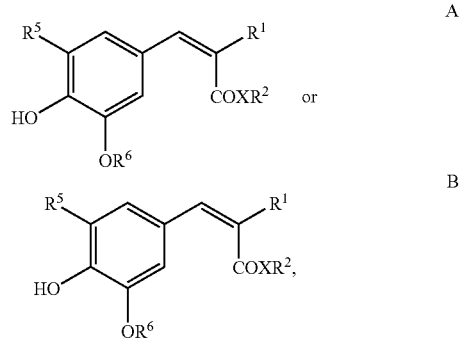

in which

R¹ can be selected from the group —C(O)CH₃, —CO₂R³, —C(O)NH₂ and —C(O)N(R⁴)₂,

X denotes O or NH,

R² denotes linear or branched alkyl having 1 to 30 C atoms,

R³ denotes linear or branched alkyl having 1 to 20 C atoms,

R⁴ in each case, independently of one another, denotes H or linear or branched alkyl having 1 to 8 C atoms, R⁵ denotes linear or branched alkyl having 1 to 8 C atoms or linear or branched alkoxy having 1 to 8 C atoms, and R⁶ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxybenzyl)malonate (for example RonaCare® AP).

Mixtures of antioxidants are likewise suitable for use in the cosmetic compositions according to the invention. Known and commercial mixtures are, for example, mixtures comprising, as active compounds, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Anti-oxidants of this type are usually employed in such compositions with compounds according to the invention in ratios in the range from 1000:1 to 1:1000, preferably in amounts of 100:1 to 1:100.

The compositions may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B₁), riboflavin (vitamin B₂), nicotinamide, vitamin C (ascorbic acid), vitamin D, ergocalciferol (vitamin D₂), vitamin E, DL-α-tocopherol, tocopherol E acetate, tocopherol hydrogensuccinate, vitamin K₁, esculin (vitamin P active ingredient), thiamine (vitamin B₁), nicotinic acid (niacin), pyridoxine, pyridoxal, pyridoxamine (vitamin B₆), pantothenic acid, biotin, folic acid and cobalamine (vitamin $B_{12}$), particularly preferably vitamin A palmitate, retinol, vitamin C and derivatives thereof, DL-α-tocopherol, tocopherol E acetate, nicotinic acid, pantothenic acid and biotin. Vitamins are usually employed here with compounds according to the invention in ratios in the range from 1000:1 to 1:1000, preferably in amounts of 100:1 to 1:100.

It has been found here that antioxidants, such as, for example, beta-carotene and tocopherol, can accelerate the conversion of the compounds of the formula I or of the formulae Ia to Id according to the invention into UV-filtering compounds. The present application therefore furthermore relates to the use of antioxidants for activating the compounds according to the invention.

Compounds preferably to be employed in accordance with the invention have—after irradiation—a UV absorption in the UV-A and/or UV-B region. The compounds to be employed in accordance with the invention include precursors of broadband UV filters, which can be employed alone or in combination with further UV filters. Other compounds according to the invention which are likewise preferred are precursors of UV filters having an absorption maximum in the boundary region between UV-B and UV-A radiation. As UV-A II filters, they can therefore advantageously supplement the absorption spectrum of commercially available UV-B and UV-A I filters.

Furthermore, preferred compounds have advantages on incorporation into the compositions:
straight-chain or branched $C_1$- to $C_{20}$-alkoxy groups, in particular the long-chain alkoxy functions, such as ethylhexyloxy groups, increase the oil solubility of the compounds
in some cases, compounds of this type are in the form of oil components and can easily be incorporated into the composition or can function as solvent for other formulation constituents.

In likewise preferred embodiments, however, the compositions may also comprise compounds of the formula I or of the formulae Ia to Id which have low solubility or are insoluble in the composition matrix. In this case, the compounds are preferably dispersed in the cosmetic composition in finely divided form.

Particularly preferred compositions can also serve as sunscreens and then also comprise UV filters in addition to the compounds according to the invention.

On use of the dibenzoylmethane derivatives, which are particularly preferred as UV-A filters, but are also used as UVB filters, or the cinnamic acid derivatives, which are employed, in particular, as UVB filters, in combination with the compounds according to the invention, an additional advantage arises: the UV-sensitive dibenzoylmethane derivatives and cinnamic acid derivatives are additionally stabilised by the presence of the compounds according to the invention. The present invention therefore furthermore relates to the use of the compounds of the formula I or of the formulae Ia to Id for the stabilisation of dibenzoylmethane derivatives and/or cinnamic acid derivatives in compositions.

In principle, all UV filters are suitable for combination with the compounds of the formula I or Ia to Id. Particular preference is given to UV filters whose physiological acceptability has already been demonstrated. Both for UVA and UVB filters, there are many proven substances known from the specialist literature, for example
benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL), benzoyl- or dibenzoylmethanes, such as 1-(4-tert-butylphenyl)-3-(4-methoxyphenyl)propane-1,3-dione (for example Eusolex® 9020) or 4-isopropyl-dibenzoylmethane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292), isopentyl 4-methoxycinnamate, for example as a mixture of the isomers (for example Neo Heliopan® E 1000), salicylate derivatives, such as 2-ethylhexyl salicylate (for example Eusolex® OS),4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25), phenylbenzimidazolesulfonic acids, such as 2-phenylbenzimidazole-5-sulfonic acid and potassium, sodium and triethanolamine salts thereof (for example Eusolex® 232), 2,2'-(1,4-phenylene)bisbenzimidazole-4,6-disulfonic acid and salts thereof (for example Neoheliopan® AP) or 2,2-(1,4-phenylene)bisbenzimidazole-6-sulfonic acid;
and further substances, such as
2-ethylhexyl 2-cyano-3,3-diphenylacrylate (for example Eusolex® OCR),
3,3'-(1,4-phenylenedimethylene)bis(7,7-dimethyl-2-oxo-bicyclo[2.2.1]hept-1-ylmethanesulfonic acid and salts thereof (for example Mexoryl® SX) and
2,4,6-trianilino-(p-carbo-2'-ethylhexyl-1'-oxy)-1,3,5-triazine (for example Uvinul® T 150)
hexyl 2-(4-diethylamino-2-hydroxybenzoyl)benzoate (for example Uvinul®UVA Plus, BASF).

The compounds mentioned in the list should only be regarded as examples. It is of course also possible to use other UV filters.

These organic UV filters are generally incorporated into cosmetic formulations in an amount of 0.5 to 10 percent by weight, preferably 1-8% by weight.

Further suitable organic UV filters are, for example,
2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®),
2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB),
α-(trimethylsilyl)-ω-[trimethylsilyl)oxy]poly[oxy(dimethyl [and approximately 6% of methyl[2-[p-[2,2-bis(ethoxycarbonyl)vinyl]phenoxy]-1-methyleneethyl] and approximately 1.5% of methyl[3-[p-[2,2-bis(ethoxycarbonyl)vinyl]phenoxy)propenyl) and 0.1 to 0.4% of (methylhydrogen]-silylene]] (n≈60) (CAS No. 207 574-74-1)
2,2'-methylenebis(6-(2H-benzotriazol-2-yl)-4-(1,1,3,3-tetramethylbutyl)phenol) (CAS No. 103 597-45-1)
2,2'-(1,4-phenylene)bis(1H-benzimidazole-4,6-disulfonic acid, mono-sodium salt) (CAS No. 180 898-37-7) and
2,4-bis{[4-(2-ethylhexyloxy)-2-hydroxy]phenyl}-6-(4-methoxyphenyl)-1,3,5-triazine (CAS No. 103 597-45-, 187 393-00-6).

2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), Further suitable UV filters are also methoxyflavones corresponding to the earlier German patent application DE-A-10232595.

Organic UV filters are generally incorporated into cosmetic formulations in an amount of 0.5 to 20 percent by weight, preferably 1-15% by weight.

Conceivable inorganic UV filters are those from the group of the titanium dioxides, such as, for example, coated titanium dioxide (for example Eusolex® T-2000, Eusolex® T-AQUA, Eusolex® T-AVO), zinc oxides (for example Sachtotec®), iron oxides or also cerium oxides. These inorganic UV filters are generally incorporated into cosmetic compositions in an amount of 0.5 to 20 percent by weight, preferably 2-10% by weight.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and potassium, sodium and triethanolamine salts thereof.

Combination of one or more of the compounds of the formula I or of the formulae Ia to Id with further UV filters enables the protective action against damaging effects of UV radiation to be optimised.

Optimised compositions may comprise, for example, the combination of the organic UV filters 4'-methoxy-6-hydroxyflavone with 1-(4-tert-butylphenyl)-3-(4-methoxyphenyl)propane-1,3-dione and 3-(4'-methylbenzylidene)-dl-camphor. This combination gives rise to broad-band protection, which can be supplemented by the addition of inorganic UV filters, such as titanium dioxide microparticles.

All the said UV filters and the compounds of the formula I or of the formulae Ia to Id can also be employed in encapsulated form. In particular, it is advantageous to employ organic UV filters in encapsulated form. In detail, the following advantages arise:

The hydrophilicity of the capsule wall can be set independently of the solubility of the UV filter or the compound of the formula I. Thus, for example, it is also possible to incorporate hydrophobic UV filters or compounds according to the invention into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or compounds according to the invention or other ingredients enables composition problems caused by the interaction of individual composition constituents with one another, such as crystallisation processes, precipitation and agglomerate formation, to be avoided since the interaction is suppressed.

It is therefore preferred for one or more of the above-mentioned UV filters or compounds of the formula I or of the formulae Ia to Id to be in encapsulated form. It is advantageous here for the capsules to be so small that they cannot be viewed with the naked eye. In order to achieve the above-mentioned effects, it is furthermore necessary for the capsules to be sufficiently stable and the encapsulated active compound (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules particularly preferably to be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions according to the invention are preferably present in amounts which ensure that the encapsulated UV filters are present in the composition in the above-indicated amounts.

The compositions according to the invention comprising at least one compound of the formula I or of the formulae Ia to Id may in addition comprise further conventional skin-protecting or skin-care active compounds. These may in principle be any active compounds known to the person skilled in the art.

Particularly preferred active compounds are pyrimidinecarboxylic acids and/or aryl oximes.

Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutical active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-up, care creams and sunscreen preparations.

Preference is given here to the use of a pyrimidinecarboxylic acid of the following formula

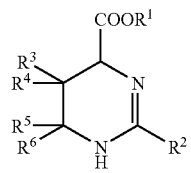

in which $R^1$ is a radical H or $C_{1-8}$-alkyl, $R^2$ is a radical H or $C_{1-4}$-alkyl, and $R^3$, $R^4$, $R^5$ and $R^6$ are each, independently of one another, a radical from the group H, OH, $NH_2$ and $C_{1-4}$-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of 100:1 to 1:100 with respect to the compounds according to the invention, with ratios in the range 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are associated with inflammation. It is known that compositions of this type can be used, for example, for the therapy of psoriasis, various forms of eczema, irritative and toxic dermatitis, UV dermatitis and further allergic and/or inflammatory diseases of the skin and skin appendages. Compositions according to the invention which, in addition to the compound of the formula I, additionally comprise an aryl oxime, preferably 2-hydroxy-5-methyllaurophenone oxime, exhibit surprising antiinflammatory suitability. The compositions here preferably comprise 0.01 to 10% by weight of the aryl oxime, it being particularly preferred for the composition to comprise 0.05 to 5% by weight of aryl oxime.

In a further, likewise preferred embodiment of the present invention, the composition comprises at least one self-tanning agent.

Advantageous self-tanning agents which can be employed are, inter alia, trioses and tetroses, such as, for example, the following compounds:

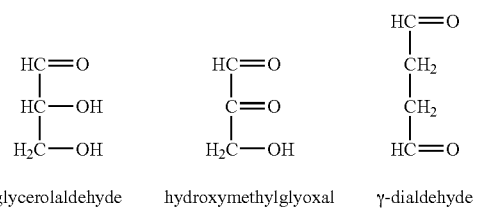

glycerolaldehyde   hydroxymethylglyoxal   γ-dialdehyde

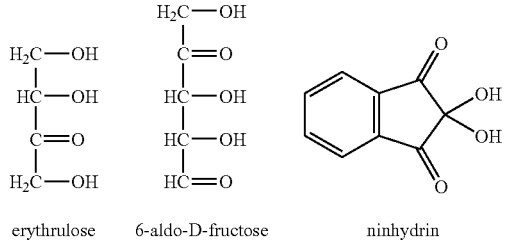

erythrulose   6-aldo-D-fructose   ninhydrin

Mention should also be made of 5-hydroxy-1,4-naphthoquinone (juglone), which can be extracted from the shells of fresh walnuts, and 2-hydroxy-1,4-naphthoquinone (lawsone), which occurs in henna leaves. The flavonoid diosmetin and its glycosides or sulfates can also be employed. These compounds can be employed here in the form of pure substances or plant extracts. Diosmetin can preferably be employed, for example, in the form of a chrysanthemum extract.

Very particular preference is given to 1,3-dihydroxyacetone (DHA), a tri-functional sugar which occurs in the human body, and derivatives thereof.

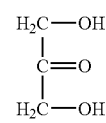

1,3-dihydroxyacetone (DHA)

The said self-tanning agents can be employed alone or as a mixture. It is particularly preferred here for DHA to be employed in a mixture with a further self-tanning agent of those mentioned above.

It has been found that the combination of self-tanning agents with the compounds according to the invention results in accelerated tanning compared with the use of the self-tanning agents alone. The present invention therefore furthermore relates to the corresponding use of the compounds according to the invention for accelerating the tanning action of self-tanning agents.

All compounds or components which can be used in the compositions are either known and commercially available or can be synthesised by known processes.

The one or more compounds of the formula I or of the formulae Ia to Id can be incorporated into cosmetic or dermatological, but also pharmaceutical compositions or into foods in a conventional manner. Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of use forms of the compositions are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower compositions. Any desired customary vehicles, auxiliaries and, if desired, further active compounds may be added to the composition.

Preferred auxiliaries originate from the group of the preservatives, antioxidants, stabilisers, solubilisers, vitamins, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up, and sunscreen, pre-sun and after-sun preparations.

The preferred composition forms include, in particular, emulsions.

Emulsions are advantageous and comprise, for example, the said fats, oils, waxes and other lipids, as well as water and an emulsifier, as usually used for a composition of this type.

The lipid phase may advantageously be selected from the following group of substances:
mineral oils, mineral waxes;
oils, such as triglycerides of capric or caprylic acid, furthermore natural oils, such as, for example, castor oil;
fats, waxes and other natural and synthetic lipids, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and hydrocarbon waxes, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride, dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane, poly(m-ethylphenylsiloxane).

Also particularly advantageous are mixtures of cyclomethicone and isotridecyl isononanoate, of cyclomethicone and 2-ethylhexyl isostearate.

The aqueous phase of the compositions optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, a mixture of the above-mentioned solvents is used. In the case of alcoholic solvents, water may be a further constituent.

Emulsions are advantageous and comprise, for example, the said fats, oils, waxes and other lipids, as well as water and an emulsifier, as usually used for a formulation of this type.

In a preferred embodiment, the compositions comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

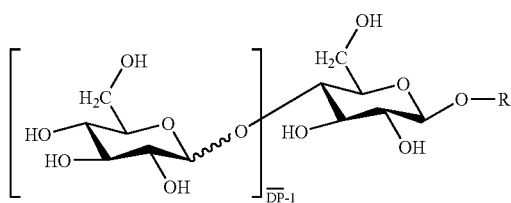

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots$$
$$= \sum \frac{p_i}{100} \cdot i$$

in which $p_1, p_2, p_3 \ldots p_i$ represent the proportion of mono-, di-, tri- ... i-fold glucosylated products in percent by weight. Advantageous in accordance with the invention is the selection of products having degrees of glucosylation of 1-2, particularly advantageously of 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used are selected from the group octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active compounds used in accordance with the invention, for example Plantaren® 1200 (Henkel KGaA), Oramix® NS 10 (Seppic).

The acyllactylates are themselves advantageously selected from the group of the substances which are distinguished by the structural formula

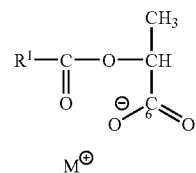

where $R^1$ denotes a branched or unbranched alkyl radical having 1 to 30 carbon atoms, and $M^+$ is selected from the group of the alkali metal ions and the group of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group of the substances which are distinguished by the structural formula

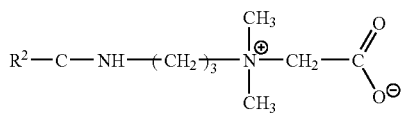

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

An advantageous coconut amphoacetate is, for example, sodium coconut amphoacetate, as available under the name Miranol® Ultra C32 from Miranol Chemical Corp.

The compositions are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions are applied to the skin and/or the hair in an adequate amount in the usual manner for cosmetics.

Cosmetic and dermatological compositions comprising at least one compound of the formula I or of the formulae Ia to Id may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer active compounds in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate,
polyethylene glycol (22) stearate, polyethylene glycol (23) stearate,
polyethylene glycol (24) stearate, polyethylene glycol (25) stearate,
polyethylene glycol (12) isostearate, polyethylene glycol (13) isostearate,
polyethylene glycol (14) isostearate, polyethylene glycol (15) isostearate,
polyethylene glycol (16) isostearate, polyethylene glycol (17) isostearate,
polyethylene glycol (18) isostearate, polyethylene glycol (19) isostearate,
polyethylene glycol (20) isostearate, polyethylene glycol (21) isostearate,
polyethylene glycol (22) isostearate, polyethylene glycol (23) isostearate,
polyethylene glycol (24) isostearate, polyethylene glycol (25) isostearate,
polyethylene glycol (12) oleate, polyethylene glycol (13) oleate,
polyethylene glycol (14) oleate, polyethylene glycol (15) oleate,
polyethylene glycol (16) oleate, polyethylene glycol (17) oleate,
polyethylene glycol (18) oleate, polyethylene glycol (19) oleate,
polyethylene glycol (20) oleate, The ethoxylated alkyl ether carboxylic acid or salt thereof used can advantageously be sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageously employed in accordance with the invention are the following:
fatty alcohols having 8 to 30 carbon atoms, monoglycerol esters of saturated and/or unsaturated, branched and/or unbranched alkanecarboxylic acids having a chain length of 8 to 24, in particular 12-18, C atoms, diglycerol esters of saturated and/or unsaturated, branched and/or unbranched alkanecarboxylic acids having a chain length of 8 to 24, in particular 12-18, C atoms, monoglycerol ethers of saturated and/or unsaturated, branched and/or unbranched alcohols having a chain length of 8 to 24, in particular 12-18, C atoms, diglycerol ethers of saturated and/or unsaturated, branched and/or unbranched alcohols having a chain length of 8 to 24, in particular 12-18, C atoms, propylene glycol esters of saturated and/or unsaturated, branched and/or unbranched alkanecarboxylic acids having a chain length of 8 to 24, in particular 12-18, C atoms, and sorbitan esters of saturated and/or unsaturated, branched and/or unbranched alkanecarboxylic acids having a chain length of 8 to 24, in particular 12-18, C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Preferred compositions are particularly suitable for protecting human skin against ageing processes and against oxidative stress, i.e. against damage caused by free radicals, as are generated, for example, by solar irradiation, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other lipid, a lower monoalcohol or lower polyol or mixtures thereof. Particularly preferred monoalcohols or polyols include ethanol, i-propanol, propylene glycol, glycerol and sorbitol.

A preferred embodiment of the invention is an emulsion in the form of a protective cream or milk which, in addition to the compound(s) according to the invention, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other lipids.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or blow-waving, in the form of a hair lacquer, permanent waving composition, colorant or bleach for the hair. Besides the compound(s) according to the invention, the composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of a composition which is characterised in that at least one compound of the formula I is mixed with a vehicle which is suitable cosmetically or dermatologically or for foods or for household products, and to the use of a compound of the formula I for the preparation of a composition having antioxidant properties.

The compositions here can be prepared with the aid of techniques which are well known to the person skilled in the art.

The mixing can result in dissolution, emulsification or dispersion of the compound according to the invention in the vehicle.

In a process which is preferred in accordance with the invention, the compound of the formula I is prepared by hydrogenation of at least one compound of the formula I en

I en where the radicals Ar, $Z^1$ and R correspond to those of the desired formula I.

An analogous situation applies to the hydrogenation of the compounds of the formula Ia en, Ib en and Id en to give the compounds of the formulae Ia to Id.

Molecular hydrogen, for example, is suitable for the hydrogenation. If molecular hydrogen is used for the hydrogenation of the compounds of the formula I en, the hydrogenation is preferably carried out in the presence of a catalyst or catalyst system.

Suitable catalysts for the hydrogenation are all common homogeneous and heterogeneous catalysts, particular preference is given to the use of at least one noble metal, preferably selected from the elements Pt, Pd and Rh, or a transition metal, such as Mo, W, Cr, but particularly Fe, Co and Ni, either individually or in a mixture. The catalyst(s) or catalyst mixture(s) here may also be employed on supports, such as carbon, activated carbon, aluminium oxide, barium carbonate, barium sulfate, calcium carbonate, strontium carbonate or kieselguhr. The metal here may also be employed in the form of the Raney compound, for example Raney nickel. If the catalysis is carried out in a homogeneous process, it is preferred for the catalyst employed to be one or more complex compounds of the said metals, such as, for example, Wilkinson's catalyst [chlorotris(triphenylphosphine) rhodium]. It is furthermore possible to employ salts of the said metals, which can be reduced in situ by a reducing agent and form a finely divided metal(0) species in situ. Suitable noble-metal salts are, for example, palladium acetate, palladium bromide and palladium chloride, suitable reducing agents are, for example, hydrogen, hydrazine, sodium borohydride and formates. In a preferred variant of the present invention, a heterogeneous catalyst is employed, it being particularly preferred for the catalyst employed in the process according to the invention to be Pd or Pt, preferably on activated-carbon support, for example 5% by weight of Pd or Pt on C.

The hydrogenation is usually carried out at a temperature in the range from 20-150° C. The hydrogenation is furthermore advantageously carried out at a hydrogen pressure of 1 to 200 bar.

Suitable solvents are protic solvents, in particular the usual protic solvents known to the person skilled in the art, such as water, lower alcohols, such as, for example, methanol, ethanol and isopropanol, and primary and secondary amines, and mixtures of protic solvents of this type, where it may be particularly preferred for the solvent employed to be water.

Suitable solvents for this reaction are furthermore also conventional aprotic solvents. For example, diethyl ether, tetrahydrofuran, benzene, toluene, acetonitrile, dimethoxyethane, dimethylformamide, dimethyl sulfoxide and N-methylpyrrolidone can be employed.

In a likewise preferred embodiment of the preparation process according to the invention, the hydrogenation is carried out in the solid state, i.e. no additional solvent is necessary.

When the reaction is complete, the work-up can be carried out by conventional methods. For example, the catalyst can be filtered off, the filtrate freed from solvent, for example by heating at reduced pressure compared with atmospheric pressure, and the resultant product purified further by conventional methods.

The further purification of the reaction products can likewise be carried out by conventional methods, for example by recrystallisation from a suitable solvent, or by chromatographic methods.

The invention furthermore relates to a process for the preparation of a compound of the formula Ib or Ic

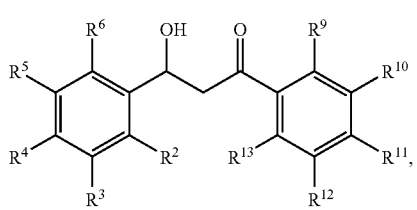

Ib

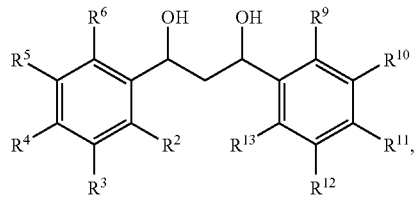

Ic where $R^4$ and $R^{11}$ each, independently of one another, denote H, a straight-chain or branched $C_1$- to $C_{20}$-alkyl group, a straight-chain or branched $C_1$- to $C_{20}$-alkoxy group or a straight-chain or branched $C_1$- to $C_{20}$-dialkylamino group, $R^6$ denotes H or a carboxylic acid, phosphoric acid, sulfonic acid, sulfuric acid or sulfone function, which may be esterified or alkylated by means of straight-chain or branched $C_1$- to $C_{20}$-alkyl groups or straight-chain or branched $C_3$- to $C_{20}$-alkenyl groups, and $R^2$, $R^3$, $R^5$, $R^9$, $R^{10}$, $R^{12}$ and $R^{13}$ denote H, characterised in that a compound of the formula Ib en

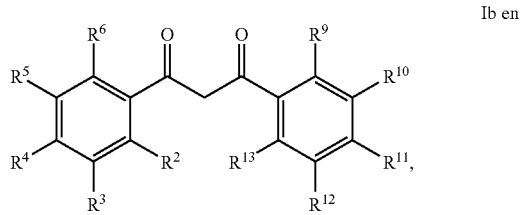

Ib en where the radicals $R^2$ to $R^6$ and $R^9$ to $R^{13}$ have a meaning mentioned above, is hydrogenated.

The compounds of the formula I or of the formulae Ia to Id can, however, also be prepared via coupling reactions, as disclosed in specific form in the examples. A general applicability of these syntheses, i.e. a reaction of an appropriately substituted aryl aldehyde with an appropriately substituted aryl ketone, is familiar to the person skilled in the art of synthesis.

General Scheme:

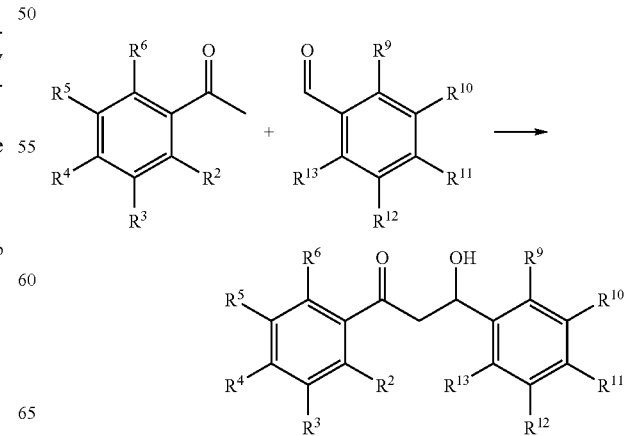

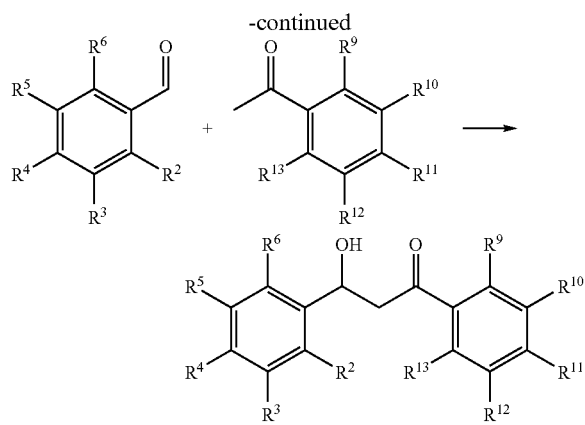

It has also been observed that compounds of the formula I or of the formulae Ia to Id can have a stabilising effect on the composition. When used in corresponding products, the latter therefore also remain stable for longer and do not change their pharmaceutical and sensory nature. In particular, the efficacy of the ingredients, for example vitamins, is retained even in the case of application over extended periods or extended storage. This is, inter alia, particularly advantageous in the case of compositions for protecting the skin against the effect of UV rays since these cosmetics are subjected to particularly high stresses by UV radiation.

The positive effects of compounds of the formula I or of the formulae Ia to Id give rise to their particular suitability for use in cosmetic or pharmaceutical compositions.

The properties of compounds of the formula I should likewise be regarded as positive for use in foods or as food supplements or as functional food. The further explanations given for foods also apply correspondingly to food supplements and functional food.

The foods which can be enriched with one or more compounds of the formula I or compounds of the formulae Ia to Id include all materials which are suitable for consumption by animals or for consumption by humans, for example vitamins and provitamins thereof, fats, minerals or amino acids. (The foods may be solid, but also liquid, i.e. in the form of a beverage). The present invention accordingly furthermore relates to the use of at least one compound of the formula I as food additive for human or animal nutrition, and to compositions which are foods or food supplements and comprise corresponding vehicles.

Foods which can be enriched with one or more compounds of the formula I are, for example, also foods which originate from a single natural source, such as, for example, sugar, unsweetened juice, squash or purée of a single plant species, such as, for example, unsweetened apple juice (for example also a mixture of different types of apple juice), grapefruit juice, orange juice, apple compote, apricot squash, tomato juice, tomato sauce, tomato purée, etc. Further examples of foods which can be enriched in accordance with the present invention with one or more compounds of the formula I are corn or cereals from a single plant species and materials produced from plant species of this type, such as, for example, cereal syrup, rye flour, wheat flour or oat bran. Mixtures of foods of this type are also suitable for being enriched with one or more compounds of the formula I, for example multivitamin preparations, mineral mixtures or sweetened juice. As further examples of foods which can be enriched in accordance with the present invention with one or more compounds of the formula I, mention may be made of food compositions, for example prepared cereals, biscuits, mixed drinks, foods prepared especially for children, such as yoghurt, diet foods, low-calorie foods or animal feeds.

The foods which can be enriched in accordance with the present invention with one or more compounds of the formula I thus include all edible combinations of carbohydrates, lipids, proteins, inorganic elements, trace elements, vitamins, water or active metabolites of plants and animals.

The foods which can be enriched in accordance with the present invention with one or more compounds of the formula I are preferably administered orally, for example in the form of meals, pills, tablets, capsules, powders, syrup, solutions or suspensions.

The foods according to the invention enriched with one or more compounds of the formula I can be prepared with the aid of techniques which are well known to the person skilled in the art.

Due to their action as antioxidants or free-radical scavengers, the compounds of the formula I are also suitable as medicament ingredient, where they support or replace natural mechanisms which scavenge free radicals in the body. The compounds according to the invention can in some cases be compared in their action with free-radical scavengers, such as vitamin C. The compounds of the formula I can be used, for example, for the preventative treatment of inflammation and allergies of the skin and in certain cases for preventing certain types of cancer. Compounds according to the invention are particularly suitable for the preparation of a medicament for the treatment of inflammation, allergies and irritation, in particular of the skin. It is furthermore possible to prepare medicaments which act as vein tonic, as agent for increasing the strength of blood capillaries, as cuperose inhibitor, as inhibitor of chemical, physical or actinic erythemas, as agent for the treatment of sensitive skin, as decongestant, as dehydration agent, as slimming agent, as anti-wrinkle agent, as stimulators of the synthesis of components of the extracellular matrix, as strengthening agent for improving skin elasticity, and as anti-ageing agent. Furthermore, compounds according to the invention which are preferred in this connection exhibit anti-allergic and anti-inflammatory and anti-irritative actions. They are therefore suitable for the preparation of medicaments for the treatment of inflammation or allergic reactions.

The invention is explained in greater detail below with reference to examples. The invention can be carried out throughout the scope claimed and is not restricted to the examples given here.

EXAMPLES

Example 1

Preparation of
2-(hydroxyphenylmethyl)-5-methoxyphenol

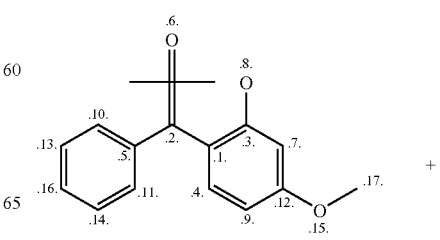

-continued

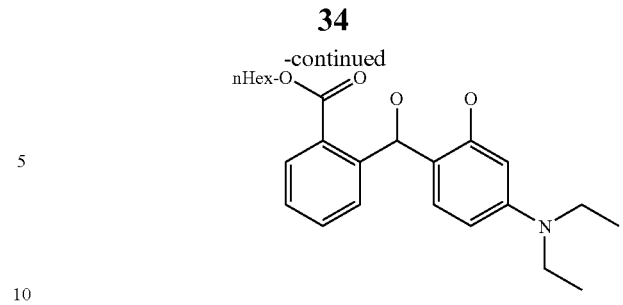

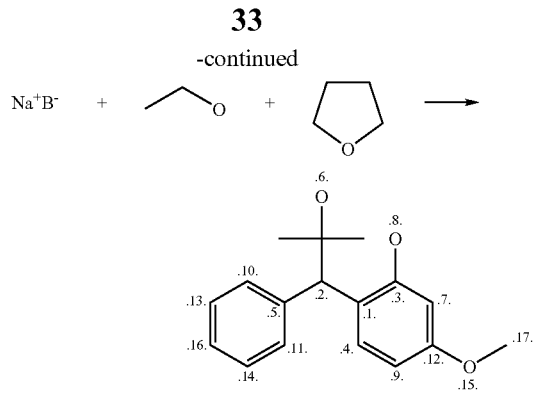

Sodium borohydride is dissolved in 75 ml of ethanol, and the starting material (2-hydroxy-4-methoxyphenyl)phenyl-methanone, dissolved in 5 ml of THF, is added dropwise over the course of about 10 min. The reaction mixture is stirred at room temperature for 1 h until all the sodium borohydride has been consumed. The solvent is removed in vacuo. The residue is partitioned in methyl t-butyl ether (MTBE)/water, and the aqueous phase is extracted a further 3 times with 50 ml of MTBE. The combined organic phases are dried over sodium sulfate, and the solvent is removed in vacuo.

Example 2

Preparation of hexyl 2-[(4-diethylamino-2-hydroxyphenyl)hydroxymethyl]benzoate (2 alternative routes)

In principle, all compounds of the formula I can be prepared analogously to Example 1 or 2. For example, the following alcohols can be obtained from the corresponding ketones:

2-(hydroxyphenylmethyl)-5-diethylaminophenol
2-(hydroxyphenylmethyl)phenol
2-(hydroxyphenylmethyl)-5-sulfophenol
2-(hydroxyphenylmethyl)-5-methoxy-4-sulfophenol
ethyl 2-[(4-diethylamino-2-hydroxyphenyl)hydroxymethyl]benzoate
ethyl hexyl 2-[(4-diethylamino-2-hydroxyphenyl)hydroxymethyl]benzoate
ethyl hexyl 2-[(2-hydroxyphenyl)hydroxymethyl]benzoate
3-hydroxy-1,3-diphenylpropan-1-one
1-(4-tert-butylphenyl)-3-hydroxy-3-phenylpropan-1-one
1-(4-tert-butylphenyl)-3-hydroxy-3-(4-methoxyphenyl)propan-1-one
3-(4-tert-butylphenyl)-3-hydroxy-1-phenylpropan-1-one
3-(4-tert-butylphenyl)-3-hydroxy-1-(4-methoxyphenyl)propan-1-one Example 3

Synthesis of 3-(4-methoxyphenyl)-3-hydroxy-1-(4-tert-butylphenyl)propan-1-one

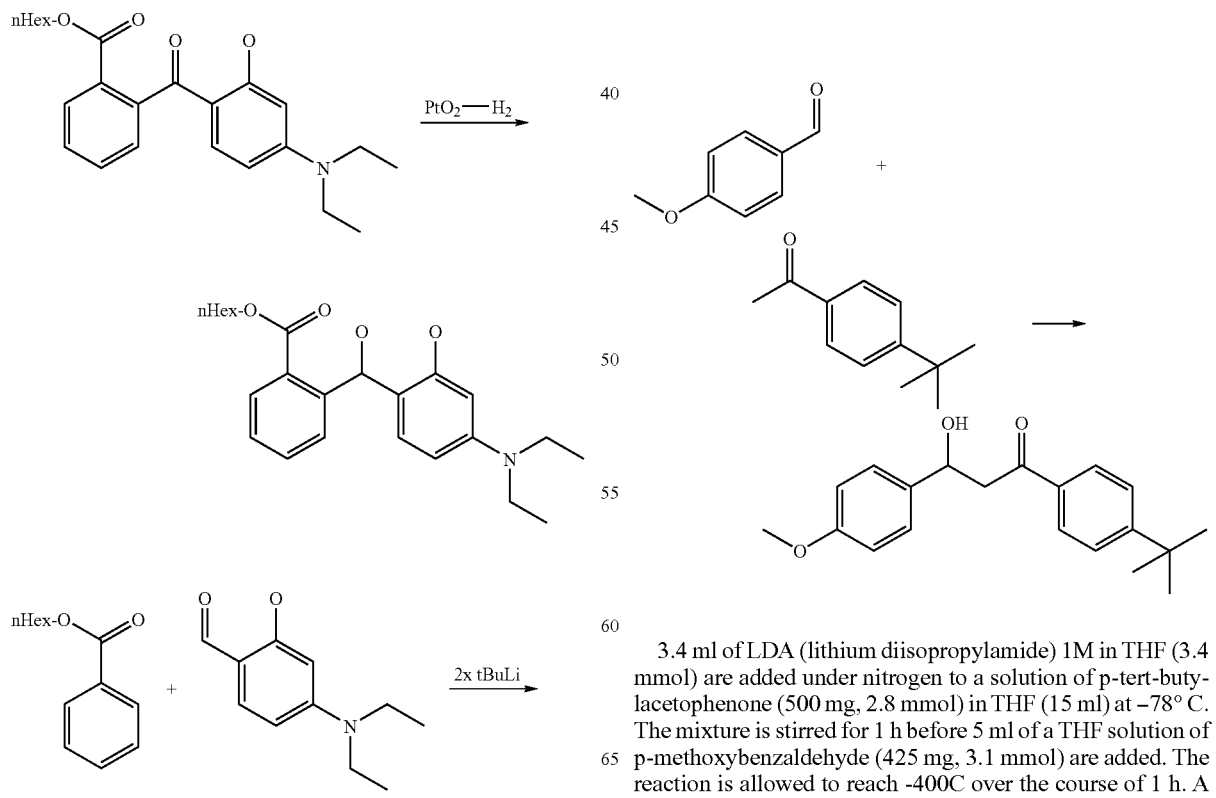

3.4 ml of LDA (lithium diisopropylamide) 1M in THF (3.4 mmol) are added under nitrogen to a solution of p-tert-butylacetophenone (500 mg, 2.8 mmol) in THF (15 ml) at −78° C. The mixture is stirred for 1 h before 5 ml of a THF solution of p-methoxybenzaldehyde (425 mg, 3.1 mmol) are added. The reaction is allowed to reach -40°C over the course of 1 h. A cold aqueous solution of NH$_4$Cl 1N is subsequently added to the reaction mixture. The resultant mixture is partitioned between water (30 ml) and dichloromethane (30 ml). The resultant aqueous phase is subsequently extracted with dichloromethane (2×30 ml). The combined organic phases are dried over MgSO$_4$. Removal of the solvent gives 3-(4-methoxyphenyl)-3-hydroxy-1-(4-tert-butylphenyl)propan-1-one.

Example 4

Synthesis of 3-(4-tert-butylphenyl)-3-hydroxy-1-(4-methoxyphenyl)propan-1-one

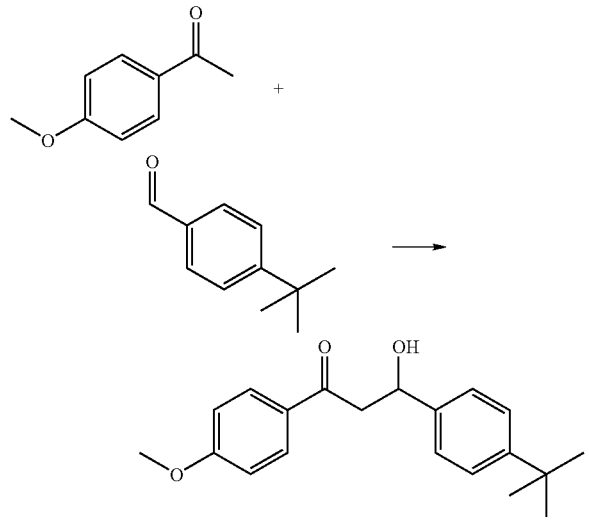

4.0 ml of LDA 1M in THF (4.0 mmol) are added under nitrogen to a solution of p-methoxyacetophenone (500 mg, 3.3 mmol) in THF (tetrahydrofuran) (15 ml) at −78° C. The mixture is stirred for 1 h before 5 ml of a THF solution of p-tert-butylbenzaldehyde (594 mg, 3.7 mmol) are added. The reaction is allowed to reach −40° C. over the course of 1 h. A cold aqueous solution of NH$_4$Cl 1N is subsequently added to the reaction mixture. The resultant mixture is partitioned between water (30 ml) and dichloromethane (30 ml). The resultant aqueous phase is subsequently extracted with dichloromethane (2×30 ml). The combined organic phases are dried over MgSO$_4$. Removal of the solvent gives 3-(4-tert-butylphenyl)-3-hydroxy-1-(4-methoxyphenyl)propan-1-one.

Example 5

Oxidation in UV Light

On irradiation by means of UV light, the UV spectrum of the compounds according to the invention as described in Example 1 or 2 changes.

The irradiation here can be carried out by means of an Atlas Sun Test CPS, xenon lamp with UV special-glass filter at a power of 95.69 W/m$^2$ in the range 290-400 nm.

After only about 60 min, significantly increased UV absorption by the compounds is evident, which increases further on longer irradiation.

Example 5a

Oxidation in UV Light in the Presence of Further Antioxidants

On irradiation with UV light, emulsions comprising compounds as described in Example 1 or 2 and beta-carotene show that the absorption by the beta-carotene (E$_{max}$ in the range 440-480 nm) in the samples according to the invention is significantly stronger compared with those which comprise only beta-carotene. Consequently, beta-carotene degradation in the emulsion according to the invention is reduced; the compounds according to the invention stabilise the beta-carotene.

Example 5b

DPPH Assay

The free-radical-reducing action of the compounds according to the invention can be demonstrated, for example, by means of the 2,2-diphenyl-1-picrylhydrazyl (DPPH) assay. 2,2-Diphenyl-1-picrylhydrazyl is a free radical which is stable in solution. The unpaired electron results in a strong absorption band at 515 nm, the solution is a dark-violet colour. In the presence of a free-radical scavenger, the electron is paired, the absorption disappears, and decolourisation proceeds stoichiometrically taking into account the electrons taken up. The absorbance is measured in a photometer. The anti-free-radical property of the substance to be tested is determined by determining the concentration at which 50% of the 2,2-diphenyl-1-picrylhydrazyl employed have reacted with the free-radical scavenger. This concentration is expressed as EC$_{50}$, a value which can be regarded as a substance property under the given measurement conditions. The substance investigated is compared with a standard (for example tocopherol). The EC$_{50}$ value here is a measure of the capacity of the respective compound to scavenge free radicals. The lower the EC$_{50}$ value, the higher the capacity to scavenge free radicals.

Procedure:

A stock solution of 2,2-diphenyl-1-picrylhydrazyl (DPPH) in ethanol is prepared (0.025 g/l of DPPH free radicals). Various concentrations of the compound to be tested are added to aliquots of this solution. The absorbance is in each case measured at 515 nm, 25° C. and 1 cm.

The EC$_{50}$ determined is the value at which 50% of the original DPPH free-radical concentration is still present. The lower this value, the higher the corresponding free-radical-reducing activity.

The reaction time required to achieve this value is indicated in the value T$_{EC50}$ (in minutes).

A detailed description, besides the DPPA assay just described, for the lipid assay (or 2,2'-azobis(2-aminopropane)=ABAP assay) or the TEAC assay (TEAC=trolox equivalent antioxidant capacity) is also found in Bünger et al, International Journal of Cosmetic Science, 2006, 28, 135-146.

The data for compound (5)=2-(hydroxyphenylmethyl)-5-methoxyphenol from Example 1 are, according to the Bünger et al. method:

DPPH assay EC50 [µmoll$^{-1}$]=1.90 (this value is not outstanding)

lipid assay: 8% (also not outstanding)

TEAC assay: 50% (this value is good)

Example 6

Photoconversion Test

Example 6a

Photoconversion Test for Compound (9)=(4-methoxyphenyl)phenylmethanol

A 4% solution of the substance in isopropyl myristate is applied at a rate of 2 μlcm$^{-2}$ to a rough Perspex support. The sample is subjected to simulated solar irradiation in a Suntester for 1 h 50 min. After irradiation, the sample is extracted with 40 ml of isopropanol and made up to a precise volume of 50 ml. Compared with an unirradiated sample, an increase in absorbance at the substance maximum at 285 nm of 0.77 absorption units arises.

Example 6b

Photoconversion Test for Compound (5) from Example 1=2-(hydroxyphenylmethyl)-5-methoxyphenol The substance is applied to roughened Perspex plates (0.75 mg/cm$^{-2}$) and irradiated under sun simulation. The dose is to be understood as the absolute, unweighted total UV irradiation dose. After each irradiation step, the UV absorption of the sample is measured against placebo (placebo=Perspex plate with glycerol). It is found that the substance increases in absorption power due to irradiation, with the starting value being no absorption at all (see FIG. 1).

Example 7

Compositions

Illustrative formulations of cosmetic compositions which comprise compounds according to Example 1 or 2 are indicated below. Corresponding compositions can be prepared in the same way with all compounds according to the invention.

In addition, the INCI names of the commercially available compounds are indicated.

UV-Pearl, OMC stands for the composition having the INCI name: Water (for EU: Aqua), Ethylhexyl Methoxycinnamate, Silica, PVP, chlorophenesin, BHT; this composition is commercially available from Merck KGaA, Darmstadt, under the name Eusolex®UV Pearl™OMC.

The other UV-Pearls indicated in the tables each have an analogous composition, with OMC being replaced by the UV filters indicated.

TABLE 1

W/O emulsions (figures in % by weight)

| | 1-1 | 1-2 | 1-3 | 1-4 | 1-5 | 1-6 | 1-7 | 1-8 | 1-9 | 1-10 |
|---|---|---|---|---|---|---|---|---|---|---|
| Titanium Dioxide | | 2 | 5 | | | | | | | 3 |
| 2-(Hydroxyphenylmethyl)-5-methoxyphenol | 5 | 3 | 2 | 1 | 2 | 1 | 2 | 1 | 1 | 1 |
| Zinc Oxide | | | | | | | | 5 | 2 | |
| UV-Pearl, OMC | 30 | 15 | 15 | 15 | 15 | 15 | 15 | 15 | 15 | 15 |
| Polyglyceryl 3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium Dioxide | 3 | | 2 | | 3 | | 2 | 5 |
| Benzylidene Malonate Polysiloxane | | 1 | 0.5 | | | | | |
| 3-(4-tert-Butylphenyl)-3-hydroxy-1-(4-methoxyphenyl)propan-1-one | 1 | 1 | 0.5 | | | | | |
| Hexyl 2-[(4-diethylamino-2-hydroxyphenyl)hydroxymethyl]benzoate | 5 | 3 | 2 | 5 | 1 | 3 | 7 | 2 |
| Polyglyceryl 3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |

TABLE 1-continued

| W/O emulsions (figures in % by weight) | | | | | | | | |
|---|---|---|---|---|---|---|---|---|
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerin | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium Dioxide | | 2 | 5 | | | | | | | 3 | 3 |
| Benzylidene Malonate Polysiloxane | | | | 1 | | | | | 1 | 1 | |
| Methylene Bis-Benzotriazolyl Tetramethylbutylphenol | | | | | 1 | 2 | 1 | | | | 1 |
| Zinc Oxide | | | | | | | | 5 | 2 | | |
| 3-(4-tert-Butylphenyl)-3-hydroxy-1-(4-methoxyphenyl)propan-1-one | 5 | 5 | 5 | 5 | 7 | 5 | 5 | 5 | 5 | 5 | 8 |
| UV-Pearl, OCR | | 10 | | | | | | | | | 5 |
| UV-Pearl, EthylhexylDimethylPABA | | | 10 | | | | | | | | |
| Di-2-ethylhexyl 4-hydroxy-3,5-dimethoxybenzylmalonate | 2 | 4 | 5 | 6 | 3 | 1 | 6 | 10 | 1 | 2 | 5 |
| UV-Pearl, Homosalate, BP-3 | | | | | | | | | 10 | | |
| UV-Pearl, Ethylhexyl Salicylate, BP-3 | | | | | | | | | | 10 | |
| BMDBM | | | | | | | | | | | 2 |
| UV-Pearl OMC, 4-Methylbenzylidene Camphor | 25 | | | | | | | | | | |
| Polyglyceryl 3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Phenethyl 3,4-dihydroxyphenyl-propionate | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

| O/W emulsions, figures in % by weight | | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium Dioxide | | 2 | 5 | | | | | | | 3 |
| Methylene Bis-Benzotriazolyl Tetramethylbutylphenol | | | | | | 1 | 2 | 1 | | |
| 1-(4-tert-Butylphenyl)-3-hydroxy-3-(4-methoxyphenyl)propan-1-one | | | | 1 | 2 | | | | 1 | 1 |
| 2-Ethylhexyl 4-Hydroxyphenyl-propionate | 1 | 3 | | 2 | | 5 | | 5 | 2 | |
| 2-(Hydroxyphenylmethyl)-5-methoxyphenol | 5 | 5 | 5 | 5 | 5 | 5 | 5 | 5 | 5 | 5 |
| Hexyl 2-[(4-diethylamino-2-hydroxyphenyl)hydroxymethyl]-benzoate | 1 | 5 | 4 | | 6 | | 7 | | 2 | 1 |
| 4-Methylbenzylidene Camphor | 2 | | 3 | | 4 | | 3 | | 2 | |
| BMDBM | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |

TABLE 2-continued

O/W emulsions, figures in % by weight

| | | | | | | | | | | |
|---|---|---|---|---|---|---|---|---|---|---|
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| *Persea Gratissima* | | | | | | | | | | |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium Dioxide | 3 | | 2 | | | | 2 | 5 |
| Benzylidene Malonate Polysiloxane | | 1 | 0.5 | | | | | |
| Hexyl 2-[(4-diethylamino-2-hydroxyphenyl)hydroxymethyl]-benzoate | 1 | 1 | 0.5 | | | | | |
| Di-2-ethylhexyl 4-Hydroxy-3,5-dimethoxybenzylmalonate | | | | | 1 | 2 | | |
| Di-2-ethylhexyl 2-Cyano-3,3-diphenyipropionate | 1 | 3 | | | 2 | | 5 | 5 |
| 5,6,7-Trihydroxyflavone | 5 | 5 | 5 | 5 | 5 | 5 | 5 | 5 |
| 3-(4-tert-Butylphenyl)-3-hydroxy-1-(4-methoxyphenyl)propan-1-one | 1 | 5 | 4 | | 6 | | 7 | |
| Zinc Oxide | | | 2 | | | | | |
| UV-Pearl, OMC | 15 | 15 | 15 | 30 | 30 | 30 | 15 | 15 |
| 4-Methylbenzylidene Camphor | | | | 3 | | | | |
| BMDBM | | | | 1 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| *Persea Gratissima* | | | | | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Tromethamine | | | | | 1.8 | | | |
| Glycerin | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium Dioxide | | | | | | | 3 | 3 | | 2 |
| Benzylidene Malonate Polysiloxane | 1 | 2 | | | | 1 | 1 | | 1 | 0.5 |
| 7,8,3',4'-Tetrahydroxyflavone | | | | 1 | 2 | | | | 1 | 1 |
| 1-(4-tert-Butylphenyl)-3-hydroxy-3-(4-methoxyphenyl)-propan-1-one | 1 | 3 | | 2 | | 5 | | 5 | 2 | |
| Di-2-ethylhexyl 2-Cyano-3,3-diphenylpropionate | 5 | 5 | 5 | 5 | 5 | 5 | 5 | 5 | 5 | 5 |
| Di-2-ethylhexyl 4-Hydroxy-3,5-dimethoxybenzylmalonate | 1 | 5 | 4 | | 6 | | 7 | | 2 | 1 |
| Phenethyl 3,4-Dihydroxy-phenylpropionate | | | 1 | 2 | 1 | | | 1 | 1 | 0.5 |
| Zinc Oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| *Persea Gratissima* | 8 | 8 | 8 | 8 | 8 | 8 | 8 | 8 | 8 | 8 |

TABLE 2-continued

| O/W emulsions, figures in % by weight | | | | | | | | | | |
|---|---|---|---|---|---|---|---|---|---|---|
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Glycerin | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

| Gels, figures in % by weight | | | | | | | | | | |
|---|---|---|---|---|---|---|---|---|---|---|
| | 3-1 | 3-2 | 3-3 | 3-4 | 3-5 | 3-6 | 3-7 | 3-8 | 3-9 | 3-10 |
| A = aqueous gel | | | | | | | | | | |
| Titanium Dioxide | | 2 | 5 | | | | | | | 3 |
| 5,6,7-Trihydroxyflavone | | | | 1 | 2 | | | | 1 | 1 |
| Di-2-ethylhexyl 4-Hydroxy-3,5-dimethoxybenzylmalonate | 1 | 3 | | 2 | | 5 | | 5 | 2 | |
| Di-2-ethylhexyl 2-Cyano-3,3-diphenylpropionate | 5 | 5 | 5 | 5 | 5 | 5 | 5 | 5 | 5 | 5 |
| Hexyl 2-[(4-diethylamino-2-hydroxyphenyl)hydroxymethyl]-benzoate | 1 | 5 | 4 | | 6 | | 7 | | 2 | 1 |
| 1-(4-tert-Butylphenyl)-3-hydroxy-3-(4-methoxyphenyl)propan-1-one | | | 1 | 1 | 2 | | | | 1 | 1 |
| Methylene Bis-Benzotriazolyl Tetramethylbutylphenol | | 1 | | | | 1 | 2 | 1 | | |
| Zinc Oxide | | | | 2 | | | | 5 | 2 | |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

| | 3-11 | 3-12 | 3-13 | 3-14 | 3-15 | 3-16 | 3-17 | 3-18 |
|---|---|---|---|---|---|---|---|---|
| a = aqueous gel | | | | A | a | a | a | a |
| Titanium Dioxide | 3 | | 2 | | | | | |
| Benzylidene Malonate Polysiloxane | | 1 | 0.5 | 1 | 2 | | | |
| Methylene Bis-Benzotriazolyl Tetramethylbutylphenol | 1 | 1 | 0.5 | | | 1 | 2 | 1 |
| Di-2-ethylhexyl 4-Hydroxy-3,5-dimethoxybenzylmalonate | | | | 1 | 2 | | | |
| 2-(Hydroxyphenylmethyl)-5-methoxy-phenol | 1 | 3 | | 2 | | 5 | | 5 |
| Di-2-ethylhexyl 2-Cyano-3,3-diphenyl-propionate | 5 | 5 | 5 | 5 | 5 | 5 | 5 | 5 |
| 6,3',4'-Trihydroxyflavone | 1 | 5 | 4 | | 6 | | 7 | |
| Zinc Oxide | | | 2 | | | | | |
| UV-Pearl, Ethylhexyl Methoxycinnamate | 15 | 15 | 15 | 15 | 15 | 15 | 15 | 15 |
| Prunus Dulcis | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |

TABLE 3-continued

| Gels, figures in % by weight | | | | | | | | | |
|---|---|---|---|---|---|---|---|---|---|
| Decyl Oleate | 2 | 2 | 2 | | | | | | |
| PEG-8 (and) Tocopherol (and) Ascorbyl Palmitate (and) Ascorbic Acid (and) Citric Acid | 0.05 | 0.05 | 0.05 | | | | | | |
| Sorbitol | 4 | 4 | 4 | 5 | 5 | 5 | 5 | 5 | |
| Polyacrylamide (and) C13-14 Isoparaffin (and) Laureth-7 | 3 | 3 | 3 | | | | | | |
| Carbomer | | | | 1.5 | 1.5 | 1.5 | 1.5 | 1.5 | |
| Propylparaben | 0.05 | 0.05 | 0.05 | | | | | | |
| Methylparaben | 0.15 | 0.15 | 0.15 | 0.15 | 0.15 | 0.15 | 0.15 | 0.15 | |
| Allantoin | | | | 0.2 | 0.2 | 0.2 | 0.2 | 0.2 | |
| Tromethamine | | | | 2.4 | 2.4 | 2.4 | 2.4 | 2.4 | |
| Water | to 100 | to 100 | to 100 | to 100 | to 100 | to 100 | to 100 | to 100 | |

| | 3-19 | 3-20 | 3-21 | 3-22 | 3-23 | 3-24 | 3-25 | 3-26 | 3-27 | 3-28 |
|---|---|---|---|---|---|---|---|---|---|---|
| 7,8,3',4'-Tetrahydroxyflavone | | | | 1 | 2 | | | | 1 | 1 |
| Hexyl 2-[(4-diethylamino-2-hydroxyphenyl)hydroxymethyl]-benzoate | 1 | 3 | | 2 | | 5 | | 5 | 2 | |
| Di-2-ethylhexyl 2-Cyano-3,3-diphenylpropionate | 5 | 5 | 5 | 5 | 5 | 5 | 5 | 5 | 5 | 5 |
| 1-(4-tert-Butylphenyl)-3-hydroxy-3-(4-methoxyphenyl)-propan-1-one | 1 | 5 | 4 | | 6 | | 7 | | 2 | 1 |
| UV-Pearl, OMC | 30 | 30 | 15 | 15 | 15 | 11 | 12 | 15 | 15 | 15 |
| Phenylbenzimidazole Sulfonic Acid | | 4 | 4 | | | | | | | |
| Sorbitol | 5 | 5 | 5 | 5 | 5 | 5 | 5 | 5 | 5 | 5 |
| Carbomer | 1.5 | 1.5 | 1.5 | 1.5 | 1.5 | 1.5 | 1.5 | 1.5 | 1.5 | 1.5 |
| Propylparaben | | | | | | | | | | |
| Methylparaben | 0.15 | 0.15 | 0.15 | 0.15 | 0.15 | 0.15 | 0.15 | 0.15 | 0.15 | 0.15 |
| Allantoin | 0.2 | 0.2 | 0.2 | 0.2 | 0.2 | 0.2 | 0.2 | 0.2 | 0.2 | 0.2 |
| Tromethamine | 2.4 | 4.2 | 4.2 | 2.4 | 2.4 | 2.4 | 2.4 | 2.4 | 2.4 | 2.4 |
| Water | to 100 | to 100 | to 100 | to 100 | to 100 | to 100 | to 100 | to 100 | to 100 | to 100 |

| | 3-29 | 3-30 | 3-31 | 3-32 | 3-33 | 3-34 | 3-35 | 3-36 |
|---|---|---|---|---|---|---|---|---|
| 1-(4-tert-Butylphenyl)-3-hydroxy-3-(4-methoxyphenyl)propan-1-one | | | | 1 | 2 | | | |
| Di-2-ethylhexyl 2-Cyano-3,3-diphenylpropionate | 1 | 3 | | 2 | | 5 | | 5 |
| Hexyl 2-[(4-diethylamino-2-hydroxyphenyl)-hydroxymethyl]benzoate | 5 | 5 | 5 | 5 | 5 | 5 | 5 | 5 |
| 5,6,7-Trihydroxyflavone | 1 | 5 | 4 | | 6 | | 7 | |
| UV-Pearl, OMC | 15 | 10 | | 10 | 10 | 10 | 15 | 10 |
| UV-Pearl, OCR | | | 10 | | | | | |
| UV-Pearl, OMC, Methylene Bis-Benzotriazolyl Tetramethylbutylphenol | | 7 | | 6 | | | | |
| UV-Pearl, Ethylhexyl Salicylate, BMDBM | | | 10 | | | | | |
| Disodium Phenyl Dibenzimidazole Tetrasulfonate | | 3 | | | | 3 | | 3 |
| Phenylbenzimidazole Sulfonic Acid | | 2 | | | 2 | 3 | | 3 |
| *Prunus Dulcis* | 5 | 5 | 5 | | | | | |
| Tocopheryl Acetate | 0.5 | 0.5 | 0.5 | | | | | |
| Caprylic/Capric Triglyceride | 3 | 3 | 3 | | | | | |
| Octyldodecanol | 2 | 2 | 2 | | | | | |
| Decyl Oleate | 2 | 2 | 2 | | | | | |
| PEG-8 (and) Tocopherol (and) Ascorbyl Palmitate (and) Ascorbic Acid (and) Citric Acid | 0.05 | 0.05 | 0.05 | | | | | |
| Sorbitol | 4 | 4 | 4 | 5 | 5 | 5 | 5 | 5 |
| Polyacrylamide (and) C13-14 Isoparaffin (and) Laureth-7 | 3 | 3 | 3 | | | | | |
| Carbomer | | | | 1.5 | 1.5 | 1.5 | 1.5 | 1.5 |
| Propylparaben | 0.05 | 0.05 | 0.05 | | | | | |
| Methylparaben | 0.15 | 0.15 | 0.15 | 0.15 | 0.15 | 0.15 | 0.15 | 0.15 |
| Allantoin | | | | 0.2 | 0.2 | 0.2 | 0.2 | 0.2 |
| Tromethamine | | | | 2.4 | 2.4 | 2.4 | 2.4 | 2.4 |
| Water | to 100 | to 100 | to 100 | to 100 | to 100 | to 100 | to 100 | to 100 |

Figure 1:
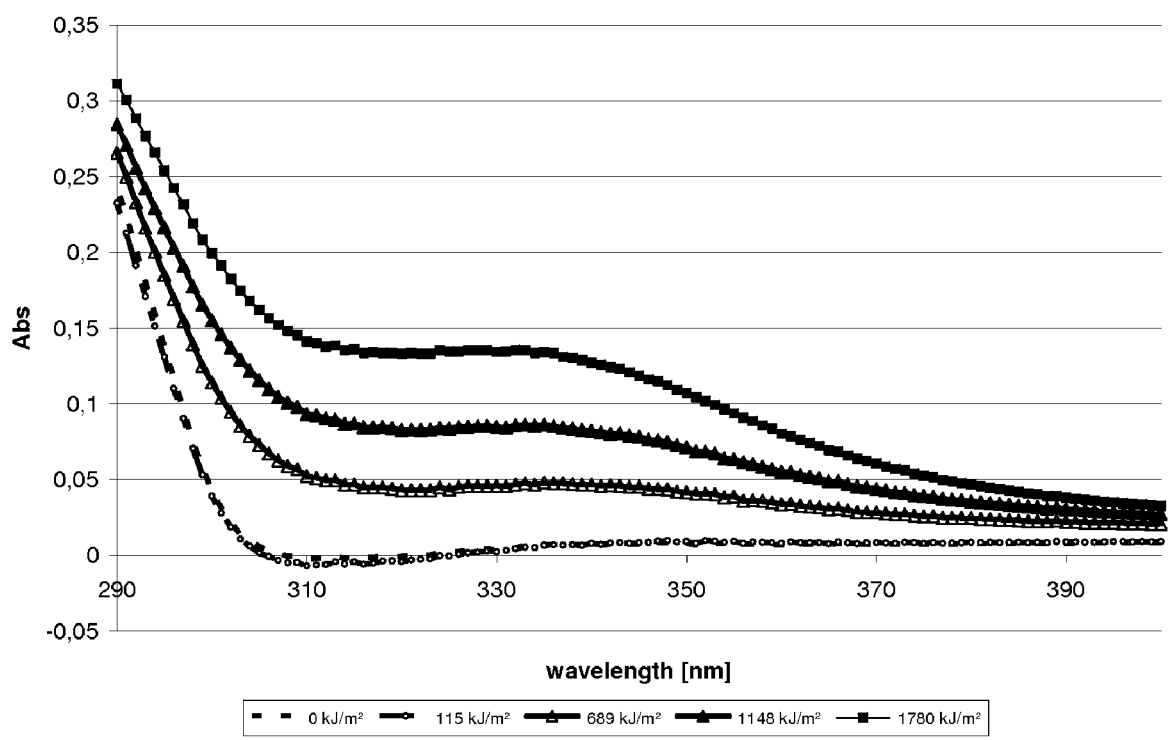
FIG. 1: illustrates results for a photoconversion test for compound (5).

The inventrion claimed is:
1. A method of providing antioxidant properties to a compound or composition, comprising adding a compound of formula I to said compound or composition

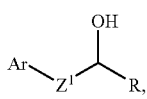

where
R stands for

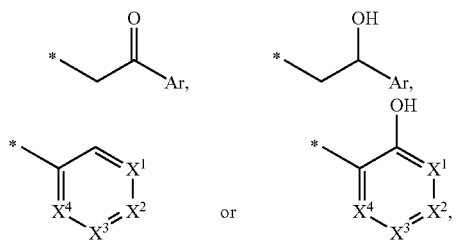

Ar each stand, independently of one another, for an unsubstituted or mono- or polysubstituted aromatic ring or condensed ring system having 6 to 18 C atoms, at least one ring of which has aromatic character, in which one or two CH groups per ring may be replaced by C=O, N, O or S and in a condensed ring system one or two $CH_2$ groups may be replaced by C=O or $C=CH_2$, $Z^1$ stands for $CR^7R^8$ or a single bond, $X^1$ to $X^4$ are each, independently of one another, C—$R^1$, O, N or S, where 2 adjacent radicals from $X^1$ to $X^4$ may together also stand for an unsubstituted or mono- or polysubstituted ring or condensed ring system having 6 to 18 C atoms, at least one ring of which optionally has aromatic character, in which one or two CH groups per ring may be replaced by C=O, N, O or S and in a condensed ring system one or two $CH_2$ groups may be replaced by C=O or $C=CH_2$, $R^1$ is selected from the group consisting of H,
straight-chain and branched $C_1$- to $C_{20}$-alkoxy groups, where the alkyl chains are each optionally interrupted by oxygen or nitrogen,
straight-chain and branched $C_1$- to $C_{20}$-alkyl groups, where the alkyl chains are each optionally interrupted by oxygen or nitrogen,
straight-chain and branched $C_3$- to $C_{20}$-alkenyl groups,
straight-chain and branched $C_1$- to $C_{20}$-hydroxyalkyl groups, where the hydroxyl group may be bonded to a primary or secondary carbon atom of the chain and the alkyl chains are each optionally interrupted by oxygen or nitrogen,
straight-chain and branched $C_1$- to $C_{20}$-hydroxyalkoxy groups, where the hydroxyl group(s) may be bonded to primary or secondary carbon atoms of the chain and the alkyl chain is optionally interrupted by oxygen,
straight-chain and branched $C_1$- to $C_{20}$-alkylamino groups, and
straight-chain and branched $C_1$- to $C_{20}$-dialkylamino groups, or $R^1$ stands for a carboxylic acid, phosphoric acid, sulfonic acid, or sulfuric acid group, which is optionally esterified resulting in a straight-chain or branched $C_1$- to $C_{20}$-alkyl or straight-chain or branched $C_3$- to $C_{20}$-alkenyl ester group of said carboxylic acid, phosphoric acid, sulfonic acid, or sulfuric acid group, $R^7$ and $R^8$ are each, independently of one another, H, OH, straight-chain or branched $C_1$- to $C_{20}$-alkoxy group, straight-chain or branched $C_1$- to $C_{20}$-alkyl group, straight-chain or branched $C_3$- to $C_{20}$-alkenyl group, straight-chain or branched $C_1$- to $C_{20}$-hydroxyalkyl group, where the hydroxyl group may be bonded to a primary or secondary carbon atom of the chain and furthermore the alkyl chain may be interrupted by oxygen, straight-chain or branched $C_1$- to $C_{20}$-hydroxyalkoxy groups, where the hydroxyl group(s) may be bonded to a primary or secondary carbon atom of the chain and the alkyl chain may also be interrupted by oxygen, or a salt thereof.

2. A method according to claim 1, wherein the compound of formula I is a compound of formula Ia, Ib, Ic or Id

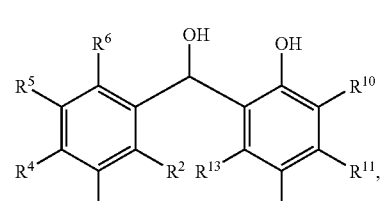

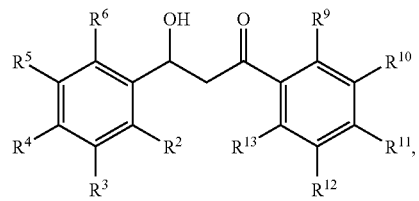

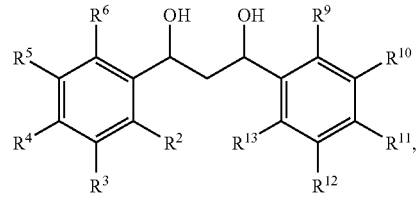

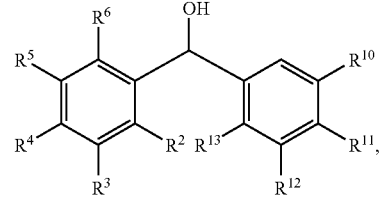

where
$R^2$ to $R^6$ and $R^9$ to $R^{13}$
are each, independently of one another, selected from the group consisting of H,
OH,
straight-chain and branched $C_1$- to $C_{20}$-alkoxy groups, where the alkyl chains are each optionally be interrupted by oxygen or nitrogen, straight-chain and branched $C_1$- to $C_{20}$-alkyl groups, where the alkyl chains are each optionally interrupted by oxygen or nitrogen, straight-chain and branched $C_3$- to $C_{20}$-alkenyl groups, straight-chain and branched $C_1$- to $C_{20}$-hydroxyalkyl groups, where the hydroxyl group may be bonded to a primary or secondary carbon atom of the chain and the alkyl chains are each optionally interrupted by oxygen or nitrogen, straight-chain and branched $C_1$- to $C_{20}$-hydroxyalkoxy groups, where the hydroxyl group(s) may be bonded to primary or secondary carbon atoms of the chain and the alkyl chain is optionally interrupted by oxygen, straight-chain and branched $C_1$- to $C_{20}$-alkylamino groups, and straight-chain and branched $C_1$- to $C_{20}$-dialkylamino groups, or $R^2$ to $R^6$ and $R^9$ to $R^{13}$ each stand, independently of one another, for a carboxylic acid, phosphoric acid, sulfonic acid, or sulfuric acid group which is optionally be esterified resulting in a straight-chain or branched $C_1$- to $C_{20}$-alkyl or straight-chain or branched $C_3$- to $C_{20}$-alkenyl ester group of said carboxylic acid, phosphoric acid, sulfonic acid, or sulfuric acid group, or a salt thereof.

3. A method according to claim 1, wherein the compound or composition to which antioxidant properties are provided is a cosmetic, dermatological or pharmaceutical composition or food or food supplement.

4. A method according to claim 2, wherein $R^4$ and $R^{11}$ are each, independently of one another, selected from the group consisting of H, straight-chain and branched $C_1$- to $C_{20}$-alkoxy groups, straight-chain and branched $C_1$- to $C_{20}$-alkyl groups and straight-chain and branched $C_1$- to $C_{20}$-dialkylamino groups.

5. A method according to claim 2, wherein $R^2$, $R^6$ and $R^{13}$ each denote H.

6. A method according to claim 2, wherein $R^3$, $R^5$, $R^9$, $R^{10}$ and $R^{12}$ denote H.

7. A method according to claim 2, wherein $R^3$ or $R^{12}$ denotes $SO_3H$ or sulfonate.

8. A method according to claim 2, wherein $R^4$ is selected from the group consisting of H, $C_1$- to $C_4$-alkoxy groups and $C_1$- to $C_4$-dialkylamino groups, $R^{11}$ is selected from the group consisting of straight-chain and branched $C_1$- to $C_6$-alkyl groups, $C_1$- to $C_4$-dialkylamino groups and $C_1$- to $C_4$-alkoxy groups.

9. A method according to claim 2, wherein $R^6$ denotes $C_1$- to $C_{10}$-alkoxycarbonyl.

10. A method according to claim 1, wherein the compound of formula I is 2-(hydroxyphenylmethyl)-5-diethylamino-phenol,
2-(hydroxyphenylmethyl)phenol,
2-(hydroxyphenylmethyl)-5-sulfophenol,
2-(hydroxyphenylmethyl)-5-methoxy-4-sulfophenol,
2-(hydroxyphenylmethyl)-5-methoxyphenol,
ethyl 2-[(4-diethylamino-2-hydroxyphenyl)phydroxymethyl]benzoate,
hexyl 2-[(4-diethylamino-2-hydroxyphenyl)hydroxymethyl]benzoate,
ethylhexyl 2-[(4-diethylamino-2-hydroxyphenyl)hydroxymethyl]benzoate,
ethylhexyl 2-[(2-hydroxyphenyl)hydroxymethyl]benzoate,
3-hydroxy-1,3-diphenylpropan-1-one, 1-(4-tert-butylphenyl)-3-hydroxy-3-phenyl-propan-1-one,
1-(4-tert-butylphenyl)-3-hydroxy-3-(4-methoxyphenyl)propan-1-one,
3-(4-tert-butylphenyl)-3-hydroxy-1-phenylpropan-1-one,
3-(4-tert-butylphenyl)-3-hydroxy-1-(4-methoxyphenyl)propan-1-one or
3-(4-methoxyphenyl)-3-hydroxy-1-(4-methoxyphenyl)propan-1-one.

11. A compound formula Ib or Ic

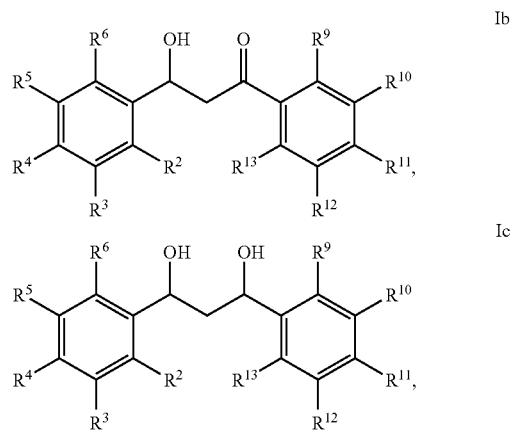

where $R^4$ and $R^{11}$ each, independently of one another, denote H, a straight-chain or branched $C_1$- to $C_{20}$-alkyl group, a straight-chain or branched $C_1$- to $C_{20}$-alkoxy group or a straight-chain or branched $C_1$- to $C_{20}$-dialkylamino group, $R^6$ denotes H or a carboxylic acid, phosphoric acid, sulfonic acid, or sulfuric acid group which is optionally esterified resulting in a straight-chain or branched $C_1$- to $C_{20}$-alkyl or straight-chain or branched $C_3$- to $C_{20}$-alkenyl ester group of said carboxylic acid, phosphoric acid, sulfonic acid, or sulfuric acid group, and $R^2$, $R^3$, $R^5$, $R^9$, $R^{10}$, $R^{12}$ and $R^{13}$ denote H, wherein 3hydroxy-1,3-diphenylpropan-1-one is excluded.

12. A compound according to claim 11, which is

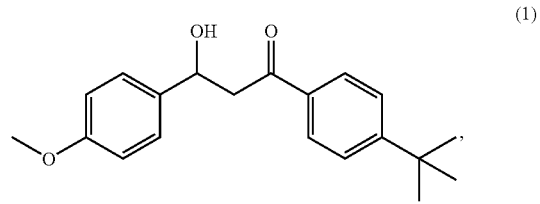

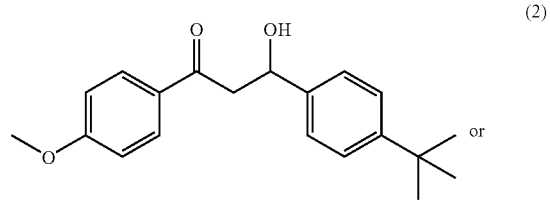

-continued (3)
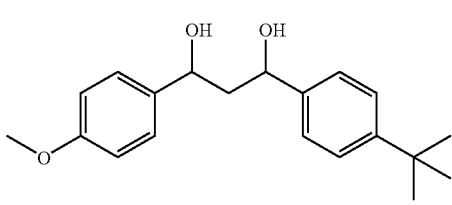

or a salt thereof.

13. A compound, which is (4)
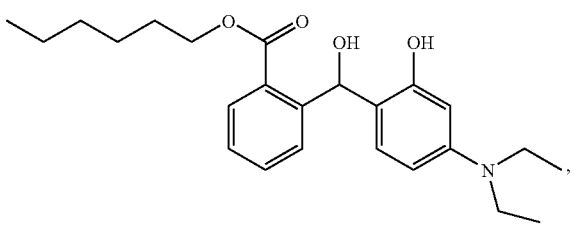

(5)
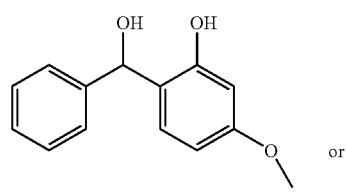

or (6)
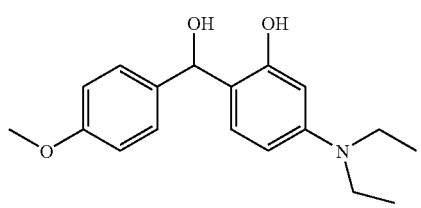

or a salt thereof.

14. A composition comprising at least one vehicle which is suitable for cosmetic or pharmaceutical application, a dermatological composition, a food or food supplement or household product and at least one compound according to claim 11.

15. A composition according to claim 14, which comprises one or more compounds of formula I in an amount of 0.01 to 20% by weight.

16. A composition according to claim 14, which comprises at least one compound of formula Ien Ien
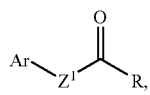

where
R stands for

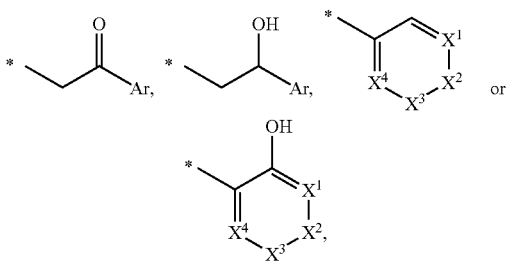

Ar each stand, independently of one another, for an unsubstituted or mono- or polysubstituted aromatic ring or condensed ring system having 6 to 18 C atoms, at least one ring of which has aromatic character, in which one or two CH groups per ring may be replaced by C=O, N, O or S and in a condensed ring system one or two $CH_2$ groups may be replaced by C=O or $C=CH_2$, $Z^1$ stands for $CR^7R^8$ or a single bond, $X^1$ to $X^4$ are each, independently of one another, C—$R^1$, O, N or S, where 2 adjacent radicals from $X^1$ to $X^4$ may together also stand for an unsubstituted or mono- or polysubstituted ring or condensed ring system having 6 to 18 C atoms, at least one ring of which optionally has aromatic character, in which one or two CH groups per ring may be replaced by C=O, N, O or S and in a condensed ring system one or two $CH_2$ groups may be replaced by C=O or $C=CH_2$, $R^1$ is selected from the group consisting of H,
straight-chain and branched to $C_1$- to $C_{20}$-alkoxy groups, where the alkyl chains are each optionally interrupted by oxygen or nitrogen,
straight-chain and branched $C_1$- to $C_{20}$-alkyl groups, where the alkyl chains are each optionally interrupted by oxygen or nitrogen,
straight-chain and branched $C_3$- to $C_{20}$-alkenyl groups,
straight-chain and branched $C_1$- to $C_{20}$-hydroxyalkyl groups, where the hydroxyl group may be bonded to a primary or secondary carbon atom of the chain and the alkyl chains are each optionally interrupted by oxygen or nitrogen,
straight-chain and branched $C_1$- to $C_{20}$-hydroxyalkoxy groups, where the hydroxyl group(s) may be bonded to primary or secondary carbon atoms of the chain and the alkyl chain is optionally interrupted by oxygen,
straight-chain and branched $C_1$- to $C_{20}$-alkylamino groups, and
straight-chain and branched $C_1$- to $C_{20}$-dialkylamino groups, or
$R^1$ stands for a carboxylic acid, phosphoric acid, sulfonic acid, or sulfuric acid group, which is optionally esterified resulting in a straight-chain or branched $C_1$- to $C_{20}$-alkyl or straight-chain or branched $C_3$- to $_{20}$-alkenyl ester group of said carboxylic acid, phosphoric acid, sulfonic acid, or sulfuric acid group,
$R^7$ and $R^8$ are each, independently of one another, H, OH, straight-chain or branched $C_1$- to $C_{20}$-alkoxy group, straight-chain or branched $C_1$- to $C_{20}$-alkyl group, straight-chain or branched $C_3$- to $C_{20}$-alkenyl group, straight-chain or branched $C_1$- to $C_{20}$-hydroxyalkyl group, where the hydroxyl group may be bonded to a primary or secondary carbon atom of the chain and furthermore the alkyl chain may be interrupted by oxygen, straight-chain or branched $C_1$- to $C_{20}$-hydroxyalkoxy groups, where the hydroxyl group(s) may be bonded to a primary or secondary carbon atom of the chain and the alkyl chain may also be interrupted by oxygen, or a salt thereof.

17. A composition according to claim 14, which is suitable for the protection of body cells against oxidative stress, and which comprises one or more further antioxidants and/or vitamins.

18. A composition according to claim 14, which comprises at least one self-tanning agent.

19. A method according to claim 1, wherein a composition is prepared which contains a compound of formula I mixed together with a vehicle which is suitable cosmetically or pharmaceutically or suitable for foods or food supplements or for household products.

20. A process for preparing a compound of formula Ib or Ic according to claim 11 comprising hydrogenating a compound of formula Ib en

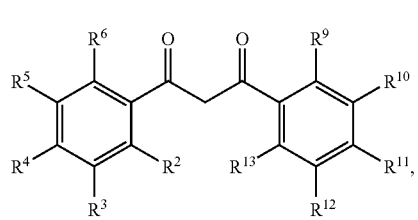

where $R^2$ to $R^6$ and $R^9$ to $R^{13}$ have a meaning as in the compound of formula Ib or Ic.

21. A method according to claim I, wherein the compound of formula I provides product protection of oxidation-sensitive formulation constituents selected from the group consisting of organic dyes, inorganic dyes, antioxidants, vitamins, perfume components, oil components, matrix constituents, emulsifiers, thickeners, film formers and surfactants.

22. A method for pigmentation control, or for lightening skin areas, comprising applying a compound of formula I to the skin

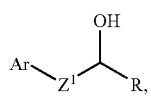

where
R stands for

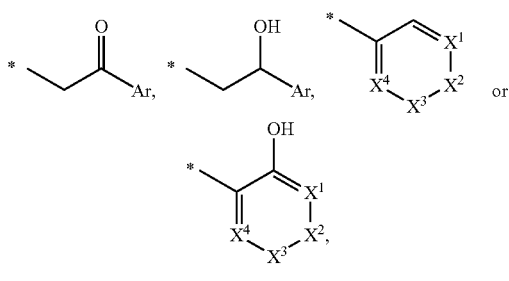

Ar each stand, independently of one another, for an unsubstituted or mono- or polysubstituted aromatic ring or condensed ring system having 6 to 18 C atoms, at least one ring of which has aromatic character, in which one or two CH groups per ring may be replaced by C═O, N, O or S and in a condensed ring system one or two $CH_2$ groups may be replaced by C═O or C═$CH_2$, $Z^1$ stands for $CR^7R^8$ or a single bond, $X^1$ to $X^4$ are each independently of one another, C—$R^1$, O, N or S, where 2 adjacent radicals from $X^1$ to $X^4$ may together also stand for an unsubstituted or mono- or polysubstituted ring or condensed ring system having 6 to 18 C atoms, at least one ring of which optionally has aromatic character, in which one or two CH groups per ring may be replaced by C═O, N, O or S and in a condensed ring system one or two $CH_2$ groups may be replaced by C═O or C═$CH_2$, $R^1$ is selected from the group consisting of H,
straight-chain and branched $C_1$- to $C_{20}$-alkoxy groups, where the alkyl chains are each optionally interrupted by oxygen or nitrogen.,
straight-chain and branched $C_1$- to $C_{20}$-alkyl groups where the alkyl chains are each optionally interrupted by oxygen or nitrogen,
straight-chain and branched $C_3$- to $C_{20}$-alkenyl groups,
straight-chain and branched $C_1$- to $C_{20}$-hydroxyalkyl groups, where the hydroxyl group may be bonded to a primary or secondary carbon atom of the chain and the alkyl chains are each optionally interrupted by oxygen or nitrogen,
straight-chain and branched $C_1$- to $C_{20}$-hydroxyalkoxy groups, where the hydroxyl group(s) may be bonded to primary or secondary carbon atoms of the chain and the alkyl chain is optionally interrupted by oxygen.,
straight-chain and branched $C_1$ to $C_{20}$-alkylamino groups, and
straight-chain and branched $C_1$- to $C_{20}$-dialkylamino groups, or $R^1$ stands for a carboxylic acid, phosphoric acid, sulfonic acid, or sulfuric acid group, which is optionally esterified resulting in a straight-chain or branched $C_1$- to $C_{20}$-alkyl or straight-chain or branched $C_3$- to $C_{20}$-alkenyl ester group of said carboxylic acid, phosphoric acid, sulfonic acid, or sulfuric acid group, $R^7$ and $R^8$ are each, independently of one another, H, OH, straight-chain or branched $C_1$- to $C_{20}$-alkoxy group, straight-chain or branched $C_1$- to $C_{20}$-alkyl group, straight-chain or branched $C_3$- to $C_{20}$-alkenyl group, straight-chain or branched $C_1$- to $C_{20}$-hydroxyalkyl group, where the hydroxyl group may be bonded to a primary or secondary carbon atom of the chain and furthermore the alkyl chain may be interrupted by oxygen, straight-chain or branched $C_1$- to $C_{20}$-hydroxyalkoxy groups, where the hydroxyl group(s) may be bonded to a primary or secondary carbon atom of the chain and the alkyl chain may also be interrupted by oxygen, or a salt thereof.

23. A method according to claim 1, wherein the compound of formula I is not 3hydroxy-1,3-diphenylpropan-1-one.

24. A method according to claim 1, wherein the compound of formula I is
2-(hydroxyphenylmethyl)-5-diethylamino-phenol,
2-(hydroxyphenylmethyl)phenol,
2-(hydroxyphenylmethyl)-5-sulfophenol,
2-(hydroxyphenylmethyl)-5-methoxy-4-sulfophenol,
2-(hydroxyphenylmethyl)-5-methoxyphenol, ethyl 2-[(4-diethylamino-2-hydroxyphenyl)hydroxymethyl]benzoate,
hexyl 2-[(4-diethylamino-2-hydroxyphenyl)hydroxymethyl]benzoate,
ethylhexyl 2-[(4-diethylamino-2-hydroxyphenyl)hydroxymethyl]benzoate,
ethylhexyl 2-[(2-hydroxyphenyl)phydroxymethyl]benzoate,
1-(4-tert-butylphenyl)-3-hydroxy-3-phenyl-propan-1-one,
1-(4-tert-butylphenyl)-3-hydroxy-3-(4-methoxyphenyl)propan-1-one,
3-(4-tert-butylphenyl)-3-hydroxy-1-phenylpropan-1-one,
3-(4-tert-butylphenyl)-3-hydroxy-1-(4-methoxyphenyl)propan-1-one or
3-(4-methoxyphenyl)-3-hydroxy-1-(4-methoxyphenyl)propan-1-one.

25. A composition comprising at least one vehicle which is suitable for cosmetic or pharmaceutical application, a dermatological composition, a food or food supplement and at least one compound according to claim 11.

* * * * *